(12) United States Patent
Phadke et al.

(10) Patent No.: US 9,610,317 B2
(45) Date of Patent: *Apr. 4, 2017

(54) 4-AMINO-4-OXOBUTANOYL PEPTIDES AS INHIBITORS OF VIRAL REPLICATION

(71) Applicant: Achillion Pharmaceuticals, Inc., New Haven, CT (US)

(72) Inventors: Avinash Phadke, Branford, CT (US); Xiangzhu Wang, Madison, CT (US); Suoming Zhang, Palo Alto, CA (US); Atul Agarwal, Hamden, CT (US)

(73) Assignee: ACHILLION PHARMACEUTICALS, INC., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/959,639

(22) Filed: Dec. 4, 2015

(65) Prior Publication Data

US 2016/0082069 A1    Mar. 24, 2016

Related U.S. Application Data

(63) Continuation of application No. 14/336,427, filed on Jul. 21, 2014, now Pat. No. 9,233,136, which is a
(Continued)

(51) Int. Cl.
| | |
|---|---|
| *A61K 38/05* | (2006.01) |
| *A61K 38/00* | (2006.01) |
| *C07K 5/02* | (2006.01) |
| *C07K 5/065* | (2006.01) |
| *C07K 5/078* | (2006.01) |

(Continued)

(52) U.S. Cl.
CPC .............. *A61K 38/05* (2013.01); *A61K 38/12* (2013.01); *A61K 45/06* (2013.01); *C07K 5/02* (2013.01); *C07K 5/06078* (2013.01); *C07K 5/06139* (2013.01); *C07K 5/06165* (2013.01);
(Continued)

(58) Field of Classification Search
None
See application file for complete search history.

(56) References Cited

U.S. PATENT DOCUMENTS

| 6,867,185 B2 | 3/2005 | Campbell et al. |
|---|---|---|
| 6,872,805 B2 | 3/2005 | Campbell et al. |

(Continued)

FOREIGN PATENT DOCUMENTS

| EP | 1881002 A1 | 1/2008 |
|---|---|---|
| WO | WO 91/01327 A1 | 2/1991 |

(Continued)

OTHER PUBLICATIONS

Andrews et al. "Pyrrolidine-5,5-trans-lactams. 2. The Use of X-ray Crystal Structure Data in the Optimization of P3 and P4 Substitutents," Organic Letters, 2002; 4(25): 4479-4482.
(Continued)

*Primary Examiner* — Thomas S Heard
(74) *Attorney, Agent, or Firm* — Knowles IP Strategies, LLC

(57) ABSTRACT

The invention provides pharmaceutical compositions comprising a compound of formula

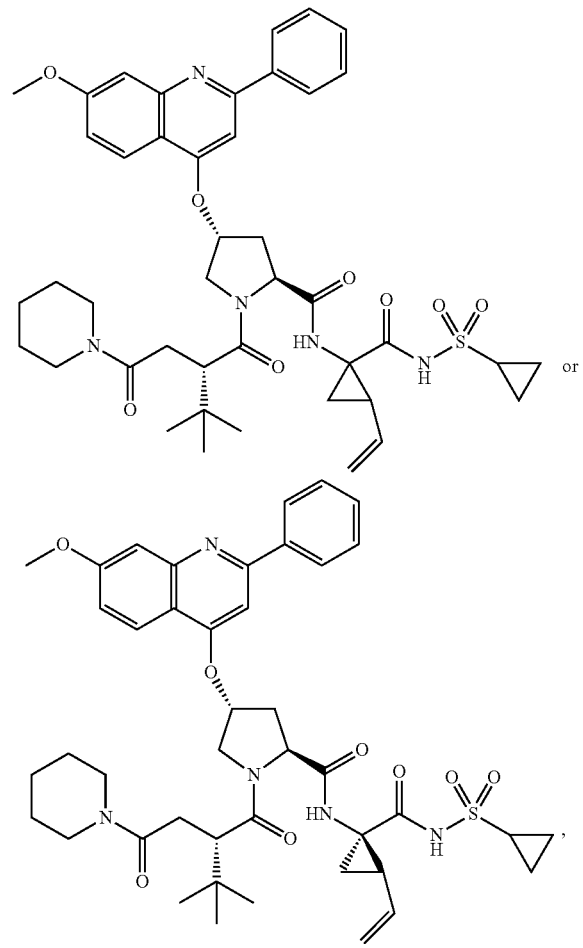

or a pharmaceutically acceptable salt or hydrate thereof. The compounds disclosed herein are potent and/or selective inhibitors of viral replication, particularly Hepatitis C virus replication, and the invention provides methods for treating Hepatitis C infections.

6 Claims, No Drawings

Related U.S. Application Data continuation of application No. 12/955,413, filed on Nov. 29, 2010, now Pat. No. 8,785,378, which is a continuation of application No. 11/777,745, filed on Jul. 13, 2007, now Pat. No. 7,906,619.

(60) Provisional application No. 60/945,786, filed on Jun. 22, 2007, provisional application No. 60/830,488, filed on Jul. 13, 2006.

(51) Int. Cl.
*C07K 5/06* (2006.01)
*C07K 5/083* (2006.01)
*A61K 38/12* (2006.01)
*A61K 45/06* (2006.01)
*C07K 5/12* (2006.01)

(52) U.S. Cl.
CPC ........ *C07K 5/06191* (2013.01); *C07K 5/0808* (2013.01); *C07K 5/12* (2013.01); *A61K 38/00* (2013.01)

(56) References Cited

U.S. PATENT DOCUMENTS

| | | |
|---|---|---|
| 6,908,901 B2 | 6/2005 | Bailey et al. |
| 6,995,174 B2 | 2/2006 | Wang et al. |
| 7,041,698 B2 | 5/2006 | Ripka et al. |
| 7,176,208 B2 | 2/2007 | Nakajima et al. |
| 7,638,529 B2 | 12/2009 | Lampilas et al. |
| 7,659,263 B2 | 2/2010 | Mizojiri et al. |
| 7,906,619 B2 | 3/2011 | Phadke et al. |
| 8,614,180 B2 | 12/2013 | Phadke et al. |
| 8,785,378 B2 | 7/2014 | Phadke et al. |
| 8,968,775 B2 | 3/2015 | Wassel et al. |
| 9,115,175 B2 | 8/2015 | Phadke et al. |
| 9,233,136 B2 | 1/2016 | Phadke et al. |
| 2003/0224977 A1 | 12/2003 | Llinas-Brunet et al. |
| 2004/0002448 A1 | 1/2004 | Tsantrizos et al. |
| 2004/0048802 A1 | 3/2004 | Ripka et al. |
| 2004/0077551 A1 | 4/2004 | Campbell et al. |
| 2004/0106559 A1 | 6/2004 | Wang et al. |
| 2004/0224900 A1 | 11/2004 | Bailey et al. |
| 2005/0020503 A1 | 1/2005 | Llinas-Brunet et al. |
| 2005/0153877 A1 | 7/2005 | Miao et al. |
| 2005/0267040 A1 | 12/2005 | Scola et al. |
| 2006/0019905 A1 | 1/2006 | Bailey et al. |
| 2006/0046965 A1 | 3/2006 | Bailey et al. |
| 2006/0046983 A1 | 3/2006 | Hudyma et al. |
| 2006/0142204 A1 | 6/2006 | Halfon et al. |
| 2006/0199773 A1 | 9/2006 | Sausker et al. |
| 2006/0281688 A1 | 12/2006 | Zhang et al. |
| 2007/0010455 A1 | 1/2007 | Hewawasam et al. |
| 2007/0093414 A1 | 4/2007 | Carini et al. |
| 2007/0099825 A1 | 5/2007 | D'Andrea et al. |
| 2009/0048297 A1 | 2/2009 | Phadke et al. |
| 2010/0216725 A1 | 8/2010 | Phadke et al. |
| 2014/0271855 A1 | 9/2014 | Chu et al. |
| 2015/0322109 A1 | 11/2015 | Phadke et al. |
| 2016/0082069 A1 | 3/2016 | Phadke et al. |
| 2016/0176847 A1 | 6/2016 | Phadke et al. |

FOREIGN PATENT DOCUMENTS

| | | |
|---|---|---|
| WO | WO 93/25574 B2 | 12/1993 |
| WO | WO 00/59929 A1 | 10/2000 |
| WO | WO 02/060926 A2 | 8/2002 |
| WO | WO 03/099274 A1 | 12/2003 |
| WO | WO 03/099316 A1 | 12/2003 |
| WO | WO 2004/043339 A2 | 5/2004 |
| WO | WO 2004/072243 A2 | 8/2004 |
| WO | WO 2004/094452 A2 | 11/2004 |
| WO | WO 2004/103996 A1 | 12/2004 |
| WO | WO 2004/113365 A2 | 12/2004 |
| WO | WO 2005/007681 A2 | 1/2005 |
| WO | WO 2005/028501 A1 | 3/2005 |
| WO | WO 2005/037214 A2 | 4/2005 |
| WO | WO 2005/046712 A1 | 5/2005 |
| WO | WO 2005/051410 A1 | 6/2005 |
| WO | WO 2005/054430 A2 | 6/2005 |
| WO | WO 2005/070955 A1 | 8/2005 |
| WO | WO 2005/073216 A2 | 8/2005 |
| WO | WO 2005/090383 A2 | 9/2005 |
| WO | WO 2005/095403 A2 | 10/2005 |
| WO | WO 2006/007700 A1 | 1/2006 |
| WO | WO 2006/007708 A1 | 1/2006 |
| WO | WO 2006/020276 A2 | 2/2006 |
| WO | WO 2006/033878 A1 | 3/2006 |
| WO | WO 2006/086381 A2 | 8/2006 |
| WO | WO 2006/096652 A2 | 9/2006 |
| WO | WO 2006/122188 A2 | 11/2006 |
| WO | WO 2007/005838 A2 | 1/2007 |
| WO | WO 2007/009109 A2 | 1/2007 |
| WO | WO 2007/009227 A1 | 1/2007 |
| WO | WO 2007/014919 A1 | 2/2007 |
| WO | WO 2007/014927 A2 | 2/2007 |
| WO | WO 2007/015824 A2 | 2/2007 |
| WO | WO 2007/030656 A1 | 3/2007 |
| WO | WO 2007/044893 A2 | 4/2007 |
| WO | WO 2008/008502 A1 | 1/2008 |
| WO | WO 2008/086161 A1 | 7/2008 |
| WO | WO 2008/095058 A1 | 8/2008 |

OTHER PUBLICATIONS

Arasappan et al. "Hepatitis C virus NS3-4A serine protease inhibitors: SAR of P2 Moiety with Improved potency," Bioorganic and Medinical Chemistry Letters, 2005; 15: 4180-4184.

Barbato et al. "Inihibitor binding induces active site stabilization of the HCV NS3 protein serine protease domain," The EMBO Journal, 2000; 19(6): 1995-1206.

Cregge et al., "Inhibition of Human Neutrophil Elastase. 4. Design, Synthesis, X-ray Crystallographic Analysis, and Structure-Activity Relationships for a Series of P2-Modified, Orally Active Peptidyl Pentafluoroethyl Ketones" Journal of Med. Chem; 41, (1998), pp. 2461-2480.

Di Marco et al. "Inhibitor of the Hepatitis C Virus NS3/4A Protease," The Journal of Biological Chemistry, 2000; 275(10): 7152-7157.

European Search Report for EU Application No. 09832542.6, International Filing Date Dec. 10, 2009, Date of Mailing Apr. 16, 2012, 5 pages.

European Search Report for EU Application No. 11169378, European Filing Date:Jul. 13, 2007; Date of Mailing:Apr. 2, 2012, 6 Pages.

European Written Opinion for European Application No. 07810457, European Filing Date: Oct. 12, 2011; Date of Mailing: Sep. 27, 2012, 4 Pages.

Goudreau et al. "Potent Inhibitors of the Hepatitis C Virus NS3 Protease: Design and Synthesis of Macrocyclic Substrate-Based B-Strand Mimics," Journal Organic Chemistry, 2004; 69: 6185-6201.

Lin et al. "In Vitro Resistance Studies of Hepatitis C Virus Serine Protease Inhibitors, VX-950 and BILN 2061," The Journal of Biological Chemistry, 2004; 279(17): 17508-17514.

Liu et al. "Hepatitis C NS3 protease inhibition by peptide-a-ketoamide inhibitors: kinectic mechanism and structure," Archives of Biochemistry and Biophysics, 2004; 421:207-216.

Llinas-Brunet et al. "A Systematic Approach to the Optimzation of Substrate-Based Inhibitors of the Hepatitis C Virus NS3 Protease: Discovery of Potent and Specific Tripeptide Inhibitors," J. Med. Chem, 2004; 47: 6584-6594.

Ontoria et al. "The Design and Enzyme-Bound Crystal Structure of Indoline Based Peptidomimetic Inhibitors of Hepatitis C Virus NS3 Protease," J. Med. Chem, 2004; 47: 6443-6446.

(56) References Cited

OTHER PUBLICATIONS

Prongay et al. "Discovery of the HCV NS3/4A Protease Inhibitor (1R,5S)-N-[3-Amino-1-(cyclobutylmethyl)-2,3-dioxopropyl]-3-[2(S)-[[[(1,1-dimethyllethyl)amino]carbonyl]amino]-3,3-dimethyl-1-oxobutyl]-6,6-dimethyl-3-azabicyclo[3.1.0]hexan-2(S)-carboxamide (Sch 5030340 II. Key Steps in Structure-Based Optimization," J. Med. Chem., 2007; 50: 2310-2318.

Rakic et al. "A Small-Molecule Probe for Hepatitis C Virus Replication the Blocks Protein Folding," Chemistry and biology, 2006; 13: 1051-1060.

Slater et al. "Pyrrolidine-5,5-trans-lactams. 4. Incorporation of a P3/P4 Urea Leads to Potent Intracellular Inhibitors of Hepatitis C Virus NS3/4A Protease," Organic Letters, 2003; 5(24): 4627-4630.

Supplemental European Search Report for EU Application No. 09832541.8, International Filing Date: Jun. 17, 2010, Date of Mailing: Jul. 27, 2012; 6 Pages.

Supplemental Search Report for European Application No. 08834325.6; European Filing Date: Sep. 24, 2008; Date of Mailing: Jan. 16, 2013; 6 Pages.

Supplementary European Search Report ; European Application No. 09832541.8, European Filing Date: Dec. 17, 2009; Date of Mailing: Jul. 27, 2012, 5 Pages.

Tsantrizos et al. "Macrocyclic Inhibitors of the NS3 Protease as Potential Therapeutic Agents of Hepatitis C Virus Infection," Agnew. Chem. Int. Ed., 2003; 42(12): 1355-1360.

Venkatraman et al. "Discovery of (1R,5S)-N[3-Amino-1-(cyclobutylmethyl)-2,3-dioxopropyl]-3-[2(S)-[[[1,1-dimethyl-lethyl) amino]carbonyl]amino]-3,3-dimethyl-1-oxobutyl]-6,6-dimethyl-3-azabicyclo[3.1.0]hexan-2(S)-carboxamide (SCH 503034), a Selective, Potent, Orally Bioavailable Hepatitis C Virus NS3 Protease Inhibitor: A Potential Therapeutic Agent for the Treatment of Hepatitis C Infection," J. Med. Chem, 2006; 49: 6074-6086.

Written Opinion of the International Searching Authority for International Patent Application No. PCT/US2009/067507; International Filing Date: Dec. 10, 2009; Date of Mailing: Aug. 24, 2010; 5 Pages.

International Search Report and Written Opinion for WO2014/152928 International Application No. PCT/US2014/028278; International Filing Date: Mar. 14, 2014; Date of Mailing :Nov. 10, 2014.

International Search Report and Written Opinion for WO2014/144087 International Application No. PCT/US2014/028348; International Filing Date: Mar. 14, 2014; Date of Mailing : Jun. 11, 2014.

International Search Report and Written Opinion for WO2010/068760 International Application No. PCT/US2009/067506.

International Search Report and Written Opinion for WO2008/106130 Application No. PCT/US2008/002524.

4-AMINO-4-OXOBUTANOYL PEPTIDES AS INHIBITORS OF VIRAL REPLICATION

CROSS REFERENCE TO RELATED APPLICATIONS

This application is a continuation of U.S. application Ser. No. 14/336,427, filed on Jul. 21, 2014, which is a continuation of U.S. application Ser. No. 12/955,413, filed on Nov. 29, 2010, now U.S. Pat. No. 8,785,378, which is a continuation of U.S. application Ser. No. 11/777,745, filed on Jul. 13, 2007, now U.S. Pat. No. 7,906,619, which claims priority from U.S. Provisional Application Nos. 60/830,488, filed Jul. 13, 2006 and 60/945,786, filed Jun. 22, 2007, all of which are hereby incorporated by reference in their entirety.

FIELD OF THE INVENTION

The present invention provides 4-amino-4-oxobutanoyl peptides, useful as antiviral agents. Certain 4-amino-4-oxobutanoyl peptides disclosed herein are potent and/or selective inhibitors of viral replication, particularly Hepatitis C virus replication. The invention also provides pharmaceutical compositions containing one or more 4-amino-4-oxobutanoyl peptides and one or more pharmaceutically acceptable carriers, excipients, or diluents. Such pharmaceutical compositions may contain 4-amino-4-oxobutanoyl peptide as the only active agent or may contain a combination of a 4-amino-4-oxobutanoyl peptide or related compound and one or more other pharmaceutically active agents. The invention also provides methods for treating viral infections, including Hepatitis C infections, in mammals.

BACKGROUND

An estimated 3% of the world's population is infected with the hepatitis C virus. Of those exposed to HCV, 80% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B-NS5A-NS5B-COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. Provisional application 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as ACH-806, VX-950 and NM 283 (prodrug of NM 107) are in clinical development for treatment of chronic HCV. Due to lack of effective therapies for treatment for certain HCV strains and the high mutation rate of HCV, new therapies are needed. The present invention fulfills this need and provides additional advantages, which are described herein.

SUMMARY OF THE INVENTION

The invention provides compounds of Formula I (shown below) and includes 4-amino-4-oxobutanoyl peptides and related compounds. Certain 4-amino-4-oxobutanoyl peptides disclosed herein possess antiviral activity. The invention provides compounds of Formula I that are potent and/or selective inhibitors of Hepatitis C virus replication. The invention also provides pharmaceutical compositions containing one or more compound of Formula I, or a salt, solvate, or acylated prodrug of such compounds, and one or more pharmaceutically acceptable carriers, excipients, or diluents.

The invention further comprises methods of treating patients suffering from certain infectious diseases by providing to such patients an amount of a compound of Formula I effective to reduce signs or symptoms of the disease or disorder. These infectious diseases include viral infections, particularly HCV infections. The invention particularly includes methods of treating human patients suffering from an infectious disease, but also encompasses methods of treating other animals, including livestock and domesticated companion animals, suffering from an infectious disease.

Methods of treatment include providing a compound of Formula I as a single active agent or providing a compound of Formula I in combination with one or more other therapeutic agents.

Thus in a first aspect the invention includes compounds of Formula I pharmaceutically acceptable salts thereof:

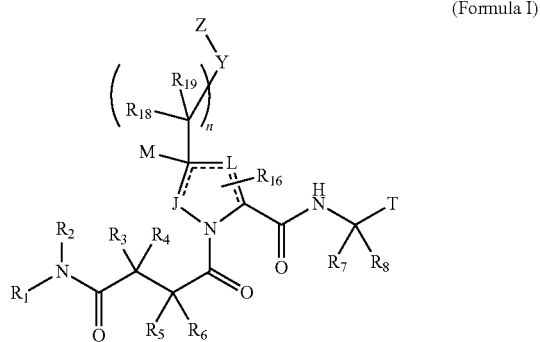

(Formula I)

Within Formula I the variables, e.g. $R_1$-$R_9$, $R_{16}$, $R_{18}$, $R_{19}$, M, Y, Z, and n, carry the definitions set forth below.

===== represents a double or single covalent bond, and the group

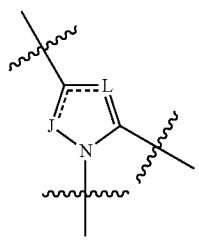

contains 0 or 1 double bonds.

$R_1$ is —$NR_{10}R_{11}$, —(C═O)$NR_{10}R_{11}$, —(C═S)$NR_{10}R_{11}$, —(C═O)$R_{12}$, —$SO_2R_{12}$, —(C═O)$OR_{12}$, —O(C═O)$R_{12}$, —$OR_{12}$, or —N(C═O)$R_{12}$, and $R_2$ is hydrogen, $C_1$-$C_6$alkyl, $C_3$-$C_7$cycloalkyl, heterocycloalkyl, (aryl)$C_0$-$C_4$alkyl.

Or, $R_1$ and $R_2$ are taken together to form an optionally substituted 5- to 7-membered heterocyclic ring containing 0 or 1 additional N, S, or O atoms, or an optionally substituted 5- to 7-membered heterocyclic ring containing 0 or 1 additional N, S, or O atoms fused to an optionally substituted 5- to 7-membered carbocyclic or heterocyclic ring.

$R_3$, $R_4$, $R_5$, $R_6$, $R_7$, and $R_8$ are independently (a) hydrogen, halogen, or amino, or (b) $C_1$-$C_6$alkyl, $C_2$-$C_6$alkenyl, ($C_3$-$C_7$cycloalkyl)$C_0$-$C_4$alkyl, ($C_3$-$C_7$cycloalkenyl)$C_0$-$C_4$alkyl, (heterocycloalkyl)$C_0$-$C_4$alkyl, $C_2$-$C_6$alkanoyl, or mono- or di-$C_1$-$C_6$alkylamino, each of which is optionally substituted.

$R_3$ and $R_4$ may be joined to form an optionally substituted 3- to 7-membered cycloalkyl ring or an optionally substituted 3- to 7-membered heterocycloalkyl ring containing 1 or 2 heteroatoms independently chosen from N, S, and O.

$R_5$ and $R_6$ may be joined to form an optionally substituted 3- to 7-membered cycloalkyl ring or an optionally substituted 3- to 7-membered heterocycloalkyl ring containing 1 or 2 heteroatoms independently chosen from N, S, and O.

$R_7$ and $R_8$ may be joined to form an optionally substituted 3- to 7-membered cycloalkyl ring or an optionally substituted 3- to 7-membered heterocycloalkyl ring containing 1 or 2 heteroatoms independently chosen from N, S, and O.

$R_5$ is a $C_7$-$C_{11}$ saturated or unsaturated hydrocarbon chain that is (i) covalently bound to $R_7$, where $R_7$ is a methylene group or $R_5$ is a $C_7$-$C_{11}$ saturated or unsaturated hydrocarbon chain that is (ii) covalently bound to an optionally substituted cycloalkyl ring formed by $R_7$ and $R_8$ being joined to from a 3- to 7-membered optionally substituted cycloalkyl ring; and $R_6$ is hydrogen, $C_1$-$C_6$alkyl, or ($C_3$-$C_7$cycloalkyl)$C_0$-$C_2$alkyl;

T is a tetrazole group attached via its carbon atom, or T is a group of the formula:

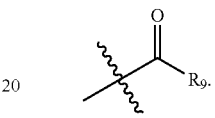

Where, $R_9$ is hydroxyl, amino, —COOH, —$NR_{10}R_{11}$, —$OR_{12}$, —$SR_{12}$, —$NR_{10}(S═O)R_{11}$, —$NR_{10}SO_2R_{11}$, —$NR_{10}SONR_{11}R_{12}$, —$NR_{10}SO_2NR_{11}R_{12}$, —(C═O)$OR_{10}$, —$NR_{10}(C═O)OR_{11}$, or —$CONR_{10}R_{11}$, or $R_9$ is $C_1$-$C_6$alkyl, $C_2$-$C_6$alkenyl, $C_2$-$C_6$alkanoyl, ($C_3$-$C_7$cycloalkyl)$C_0$-$C_4$alkyl, ($C_3$-$C_7$cycloalkenyl)$C_0$-$C_4$alkyl, ($C_3$-$C_7$cycloalkyl)$CH_2SO_2$—, ($C_3$-$C_7$cycloalkyl)$CH_2SO_2NR_{10}$—, (heterocycloalkyl)$C_0$-$C_4$alkyl, (aryl)$C_0$-$C_2$alkyl, or (5- to 10-membered heteroaryl)$C_0$-$C_2$alkyl, each of which is optionally substituted.

Or, $R_9$ is a phosphonate of the formula

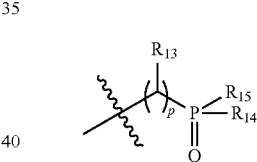

Or, $R_9$ is $R_XXC_0$-$C_4$alkyl-, where X is —(C═O)NH—, —NH(C═O)— and $R_X$ is aryl or heteroaryl, or $R_9$ is —CH($R_Y$)($C_3$-$C_7$cycloalkyl), —$SO_2CH(R_Y)(C_3$-$C_7$cycloalkyl), or —$NR_{10}SO_2CH(R_Y)(C_3$-$C_7$cycloalkyl), where $R_Y$ is halogen or $R_Y$ is $C_1$-$C_6$alkyl, $C_2$-$C_6$alkanoyl, ($C_3$-$C_7$cycloalkyl)$C_0$-$C_4$alkyl, ($C_4$-$C_7$cycloalkenyl)$C_0$-$C_4$alkyl, (aryl)$C_0$-$C_4$alkyl, (aryl)$C_0$-$C_4$alkoxy, (heterocycloalkyl)$C_0$-$C_2$alkyl, or (5- to 10-membered heteroaryl)$C_0$-$C_4$alkyl, each of which is optionally substituted.

$R_{10}$, $R_{11}$, and $R_{12}$ are independently at each occurrence hydrogen, or $C_1$-$C_6$alkyl, $C_2$-$C_6$alkenyl, $C_2$-$C_6$alkynyl, (aryl)$C_0$-$C_2$alkyl, ($C_3$-$C_7$cycloalkyl)$C_0$-$C_2$alkyl, ($C_3$-$C_7$cycloalkenyl)$C_0$-$C_2$alkyl, (heterocycloalkyl)$C_0$-$C_2$alkyl, or (5- to 10-membered heteroaryl)$C_0$-$C_2$alkyl, each of which is optionally substituted.

$R_{13}$ is hydrogen or $C_1$-$C_2$alkyl.

$R_{14}$ and $R_{15}$ are independently hydrogen, hydroxyl, or $C_1$-$C_2$alkyl.

n is 0, 1, or 2.

M is hydrogen, halogen, hydroxyl, $C_1$-$C_2$alkyl, or $C_1$-$C_2$alkoxy.

Y is absent, $CR_{18}R_{19}$, $NR_{20}$, S, O, —O(C═O)($NR_{20}$)—, $NH(C═O)(NR_{20})$—, $NH(S═O)(NR_{20})$—, or —O(C═O)—; or Y is taken together with one of J, L, or M to form a ring.

J is CH$_2$ or J is taken together with Y to form a 3- to 7-membered carbocyclic or heterocyclic ring, which ring is substituted with 0 or 1 or more substituents independently chosen from halogen, hydroxy, amino, cyano, C$_1$-C$_2$alkyl, C$_1$-C$_2$alkoxy, C$_1$-C$_2$alkoxy, trifluoromethyl, and trifluoromethoxy; when J is taken together with Y to form a ring Z may be absent.

L is CH$_2$ or L is taken together with Y to form a 3- to 7-membered carbocyclic or heterocyclic ring, which ring is substituted with 0 or 1 or more substituents independently chosen from halogen, hydroxy, amino, cyano, C$_1$-C$_2$alkyl, C$_1$-C$_2$alkoxy, C$_1$-C$_2$alkoxy, trifluoromethyl, and trifluoromethoxy; when L is taken together with Y to form a ring Z may be absent.

Z is (mono- or bicyclic aryl)C$_0$-C$_2$alkyl or (mono- or bicyclic heteroaryl)C$_0$-C$_2$alkyl, each of which Z is substituted with 0 or 1 or more substituents independently chosen from halogen, hydroxyl, amino, cyano, —CONH$_2$, —COOH, —SO$_2$NR$_{11}$R$_{12}$, —(C═O)NR$_{11}$R$_{12}$, —NR$_{11}$(C═O)R$_{12}$, C$_1$-C$_4$alkyl, C$_2$-C$_4$alkanoyl, C$_1$-C$_4$alkoxy, C$_1$-C$_4$alkylthio, mono- and di-C$_1$-C$_4$alkylamino, C$_1$-C$_4$alkylester, C$_1$-C$_2$haloalkyl, and C$_1$-C$_2$haloalkoxy, and 0 or 1 (C$_3$-C$_7$cycloalkyl)C$_0$C$_2$alkyl, (phenyl)C$_0$-C$_2$alkyl, (phenyl)C$_0$-C$_2$alkoxy, (5- or 6-membered heteroaryl)C$_0$-C$_2$alkyl, (5- or 6-membered heteroaryl)C$_0$-C$_2$alkoxy, naphthyl, indanyl, (5- or 6-membered heterocycloalkyl)C$_0$-C$_2$alkyl, or 9- or 10-membered bicyclic heteroaryl, each of which is substituted with 0, 1, or 2 substituents independently chosen from:

(c) halogen, hydroxyl, amino, cyano, nitro, —COOH, —CONH$_2$, CH$_3$(C═O)NH—, ═NOH, C$_1$-C$_4$alkyl, C$_1$-C$_4$alkoxy, C$_1$-C$_4$hydroxyalkyl, mono- and di-C$_1$-C$_4$alkylamino, —NR$_8$SO$_2$R$_{11}$, —C(O)OR$_{11}$, —NR$_8$COR$_{11}$, —NR$_8$C(O)OR$_{11}$, trifluoromethyl, and trifluoromethoxy, and (d) phenyl and 5- or 6-membered heteroaryl, each of which is substituted with 0 or 1 or more of halogen, hydroxyl, C$_1$-C$_4$alkyl, and C$_1$-C$_2$alkoxy.

R$_{16}$ represents 0 to 4 substituents is independently chosen at from halogen, C$_1$-C$_2$alkyl, and C$_1$-C$_2$alkoxy.

R$_{18}$ and R$_{19}$ are independently hydrogen, hydroxyl, halogen, C$_1$-C$_2$alkyl, C$_1$-C$_2$alkoxy, C$_1$-C$_2$haloalkyl, or C$_1$-C$_2$haloalkoxy.

R$_{20}$ is hydrogen, C$_1$-C$_2$alkyl, C$_1$-C$_2$haloalkyl, or C$_1$-C$_2$haloalkoxy.

Certain compounds of Formula I disclosed herein exhibit good activity in an HCV replication assay, such as the HCV replicon assay set forth in Example 3, which follows. Preferred compounds of Formula I exhibit an EC$_{50}$ of about 40 micromolar or less, or more preferably an EC$_{50}$ of about 10 micromolar or less; or still more preferably an EC$_{50}$ of about 5 nanomolar or less in an HCV replicon replication assay

DETAILED DESCRIPTION OF THE INVENTION

Chemical Description and Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well hydrates of the compound and all pharmaceutically acceptable salts of the compound.

The term "4-amino-4-oxobutanoyl peptides" encompasses all compounds that satisfy Formula I, including any enantiomers, racemates and stereoisomers, as well as all pharmaceutically acceptable salts of such compounds. The phrase "a compound of Formula I" includes all forms of such compounds, including salts and hydrates, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of the invention), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

A dash ("-") that is not between two letters or symbols is used to indicate a point of attachment for a substituent. For example, —$(CH_2)C_3$-$C_8$cycloalkyl is attached through carbon of the methylene ($CH_2$) group.

"Alkanoyl" indicates an alkyl group as defined herein, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

A bond represented by a combination of a solid and dashed line, ie. ====, may be either a single or double bond.

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having from 1 to about 6 carbon atoms. Other embodiments include alkyl groups having from 1 to 8 carbon atoms, 1 to 4 carbon atoms or from 1 to 2 carbon atoms, e.g. $C_1$-$C_8$alkyl, $C_1$-$C_4$alkyl, and $C_1$-$C_2$alkyl. When $C_0$-$C_n$alkyl is used herein in conjunction with another group, for example, (aryl)$C_0$-$C_4$ alkyl, the indicated group, in this case aryl, is either directly bound by a single covalent bond ($C_0$), or attached by an alkyl chain having the specified number of carbon atoms, in this case from 1 to about 4 carbon atoms. $C_0$-$C_n$alkyl is used in conjunction with heteroaryl, aryl, phenyl, cycloalkyl, and heterocycloalkyl, e.g., (5- to 10-membered heteroaryl)$C_0$-$C_2$alkyl, (aryl)$C_0$-$C_2$alkyl, (phenyl)$C_0$-$C_2$alkyl, ($C_3$-$C_7$cycloalkyl)$C_0$-$C_4$alkyl, and (heterocycloalkyl)$C_0$-$C_4$alkyl. Examples of alkyl include, but are not limited to, methyl, ethyl, n-propyl, isopropyl, n-butyl, 3-methylbutyl, t-butyl, n-pentyl, and sec-pentyl.

"Alkenyl" indicates a straight or branched hydrocarbon chain comprising one or more unsaturated carbon-carbon double bonds, which may occur in any stable point along the chain. Alkenyl groups described herein have the indicated number of carbon atoms. E.g. $C_2$-$C_6$alkenyl indicates an alkenyl group of from 2 to about 6 carbon atoms. When no number of carbon atoms is indicated, alkenyl groups described herein typically have from 2 to about 12 carbon atoms, though lower alkenyl groups, having 8 or fewer carbon atoms, are preferred. Examples of alkenyl groups include ethenyl, propenyl, and butenyl groups.

"Alkynyl" indicates a straight or branched hydrocarbon chain comprising one or more carbon-carbon triple bonds, which may occur in any stable point along the chain. Alkenyl groups described herein have the indicated number of carbon atoms. E.g. $C_2$-$C_6$alkynyl indicates an alkynyl group of from 2 to about 6 carbon atoms. When no number of carbon atoms is indicated, alkynyl groups described herein typically have from 2 to about 12 carbon atoms, though lower alkynyl groups, having 8 or fewer carbon atoms, are preferred.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. When "$C_0$-$C_n$alkoxy" is used in with another group, for example, (heteroaryl)$C_0$-$C_4$ alkoxy, the indicated group, in this case heteroaryl, is either attached via a covalently bound oxygen bridge ($C_0$alkoxy), or attached by an alkoxy group having the specified number of carbon atoms, in this case from 1 to about 4 carbon atoms, that is covalently bound to the group it substitutes via the alkoxy oxygen atom.

The term "alkylester" indicates an alkyl group as defined herein attached through an ester linkage. The ester linkage may be in either orientation, e.g. a group of the formula —O(C=O)alkyl or a group of the formula —(C=O) Oalkyl.

"Alkylthio" means alkyl-S—, where the alkyl group is an alkyl group as defined herein having the indicated number of carbon atoms and the point of attachment of the alkythio substituent is on the sulfur atom. An exemplary alkylthio group is methylthio.

"Aryl" indicates an aromatic group containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxyphenyl group. Aryl groups include, for example, phenyl, naphthyl, including 1-naphthyl and 2-naphthyl, and biphenyl.

In the term "(aryl)alkyl," aryl and alkyl are as defined above, and the point of attachment is on the alkyl group. "(Aryl)$C_0$-$C_4$alkyl" indicates an aryl group that is directly attached via a single covalent bond (aryl)$C_0$alkyl or attached through an alkyl group having from 1 to about 4 carbon atoms. Examples of (aryl)alkyl groups include piperonyl and (phenyl)alkyl groups such as benzyl and phenylethyl. Similarly, the term "(aryl)$C_0$-$C_4$alkoxy" indicates an aryl group that is directly attached to the molecule it substitutes via an oxygen bridge, e.g. (aryl)$C_0$alkoxy, or covalently bound to an alkoxy group having from 1 to 4 carbon atoms.

A "carbocyclic ring" is a saturated, partially unsaturated, or aromatic cyclic group containing only carbon ring atoms. A "5- to 7-membered carbocyclic ring" has from 5 to 7 carbon ring atoms. Unless otherwise indicated, the carbocyclic ring may be attached to its pendant group at any carbon atom that results in a stable structure. When indicated the carbocyclic rings described herein may be substituted on any available ring carbon if the resulting compound is stable. Carbocyclic rings include, cycloalkyl groups, such as cyclopropyl and cyclohexyl; cycloalkenyl groups, such as cyclohexenyl, bridged cycloalkyl groups; and aryl groups, such as phenyl.

"Cycloalkyl" saturated hydrocarbon ring group, having the specified number of carbon atoms. Monocyclic cycloalkyl groups typically have from 3 to about 8 carbon ring atoms or from 3 to about 7 carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane. Likewise "cycloalkenyl" is a hydrocarbon ring group having the indicated number of carbon atoms and at least carbon-carbon double between ring carbon atoms.

The terms "(cycloalkyl)$C_0$-$C_n$alkyl" and "(cycloalkenyl) $C_0$-$C_n$alkyl" indicate a substituent in which the cycloalkyl or cycloalkenyl and alkyl are as defined herein, and the point of attachment of the (cycloalkyl)alkyl group or (cycloalkenyl)alkyl group to the molecule it substitutes is either a single covalent bond, ($C_0$alkyl) or on the alkyl group.

(Cycloalkyl)alkyl encompasses, but is not limited to, cyclopropylmethyl, cyclohexylmethyl, and cyclohexylmethyl.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates any of fluoro, chloro, bromo, and iodo.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. "Tricyclic heteroaryl" groups contain three fused rings, at least one of which is a heteroaryl ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

The term "heterocycloalkyl" indicates a saturated monocyclic group having the indicated number of ring atoms and containing from 1 to about 3 heteroatoms chosen from N, O, and S, with remaining ring atoms being carbon, or a saturated bicyclic ring system having at least one N, O, or S ring atom with the remaining atoms being carbon. Monocyclic heterocycloalkyl groups usually have from 4 to about 8 ring atoms. In some embodiments monocyclic heterocyloalkyl groups have from 5 to 7 ring atoms. Bicyclic heterocycloalkyl groups typically have from about five to about 12 ring atoms. Examples of heterocycloalkyl groups include morpholinyl, piperazinyl, piperidinyl, and pyrrolidinyl groups.

The term "(heterocycloalkyl)alkyl" indicates a saturated substituent in which the heterocycloalkyl and alkyl are as defined herein, and the point of attachment of the (heterocycloalkyl)alkyl group to the molecule it substitutes is on the alkyl group. This term encompasses, but is not limited to, piperidylmethyl, piperazinylmethyl, and pyrrolidinylmethyl.

The term "heterocyclic ring" indicates a saturated, partially unsaturated, or aromatic cyclic group having the indicated number of ring atoms, typically from 5 to 8 ring atoms, and containing from 1 to about 4 heteroatoms chosen from N, O, and S, with remaining ring atoms being carbon, or bicyclic saturated, partially unsaturated, or aromatic heterocylic or tricyclic ring system, containing at least 1 heteroatom in the multiple ring system chosen from N, O, and S and containing up to about 4 heteroatoms independently chosen from N, O, and S in each ring of the multiple ring system. Bicyclic and tricyclic rings have the indicated number of ring atoms with bicyclic heterocyclic ring systems typically having from 7 to 11 ring atoms and tricyclic systems from 10 to 15 ring atoms. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples of heterocyclic groups include, but are not limited to 1,1-dioxo-thieno-tetrahydrothiopyranyl, 1,1-dioxothiochromanyl, 1,4-dioxanyl, 5-pteridinyl, tetrahydroindazolyl, azetidinyl, benzimidazolyl, benzisoxazinyl, benzodioxanyl, benzodioxolyl, benzofurazanyl, benzoisoxolyl, benzopyranyl, benzopyrazolyl, benzotetrahydrofuranyl, benzotetrahydrothienyl, benzothiopyranyl, benzotriazolyl, benzoxazinyl, benzoxazolinonyl, benzoxazolyl, beta-carbolinyl, carbazolyl, carbolinyl, chromanonyl, chromanyl, cinnolinyl, coumarinyl, dihydroazetidinyl, dihydrobenzisothiazinyl, dihydrobenzisoxazinyl, dihydrobenzodioxinyl, dihydrobenzofuranyl, dihydrobenzoimidazolyl, dihydrobenzothiophenyl, dihydrobenzoxazolyl, dihydrocoumarinyl, dihydroindolyl, dihydroisocoumarinyl, dihydroisooxazolyl, dihydroisoquinolinonyl, dihydroisothiazolyl, dihydrooxadiazolyl, dihydropyrazinyl, dihydropyrazolyl, dihydropyridinyl, dihydropyrimidinyl, dihydropyrrolyl, dihydroquinolinonyl, dihydroquinolinyl, dihydrotetrazolyl, dihydrothiadiazolyl, dihydrothiazolyl, dihydrothienyl, dihydrotriazolyl, hexahydroazepinyl, imidazopyrazinyl, imidazopyridazinyl, imidazopyridinyl, imidazopyridyl, imidazopyrimidinyl, imidazothiadiazolyl, imidazothiazolyl, imidazothiophenyl, indolinyl, indolizinyl, isobenzotetrahydrofuranyl, isobenzotetrahydrothienyl, isobenzothienyl, isochromanyl, isocoumarinyl, isoindolinonyl, isoindolinyl, isoquinolyl, isothiazolyl, isoxazolyl, methylenedioxybenzyl, naphthyridinyl, oxadiazolyl, oxazolopyridinyl, oxazolyl, oxetanyl, oxopiperidinyl, oxopyrazolyl, oxopyridinyl, phenothiazinyl, phenoxazinyl, phthalazinyl, purinyl, pyrazinyl, pyrazolopyrazinyl, pyrazolopyridazinyl, pyrazolopyridyl, pyrazolopyrimidinyl, pyrazolothiophenyl, pyrazolotriazinyl, pyridazinyl, pyridopyridinyl, quinazolinyl, quinolinyl, quinoxalinyl, tetrahydrofuranyl, tetrahydroimidazopyrazinyl, tetrahydroimidazopyridazinyl, tetrahydroimidazopyridinyl, tetrahydroimidazopyrimidyl, tetrahydroisoquinolinyl, tetrahydropyranyl, tetrahydropyrazolopyrazinyl, tetrahydropyrazolopyridinyl, tetrahydropyrazolopyrimidyl, tetrahydroquinolinyl, tetrahydrothienyl, tetrahydrotriazolopyrimidyl, tetrahydrotriazolopyrazinyl, tetrahydrotriazolopyridazinyl, tetrahydrotriazopyridinyl, tetrazolopyridyl, tetrazolyl, thiadiazolyl, thieno-tetrahydrothiopyranyl, thienyl, thiochromanyl, triazinyl, triazolopyrazinyl, triazolopyridazinyl, triazolopyridyl, triazolopyrimidinyl, triazolothiophenyl, and where possible, N-oxides thereof.

"Hydroxyalkyl" is an alkyl group having the indicated number of carbon atoms and substituted with at least one hydroxyl substituent. Where indicated, the hydroxyalkyl group may be further substituted.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

"Mono- and/or di-alkylcarboxamide" indicates a monoalkylcarboxamide group of formula (alkyl1)-NH—(C=O)— or a dialkylcarboxamide group of the formula (alkyl1)(alkyl2)-N—(C=O)— in which the point of attachment of the mono- or dialkylcarboxamide substituent to the molecule it substitutes is on the carbon of the carbonyl group. The term "mono and/or di-alkylcarboxamide" also includes groups of the formula (alkyl1)(C=O)NH— and (alkyl1)(C=O) (alkyl2)N— in which the point of attachment is the nitrogen atom. The groups alkyl1 and alkyl2 are independently chosen alkyl groups having the indicated number of carbon atoms.

"Oxo," means a keto group (C=O). An oxo group that is a substituent of a nonaromatic carbon atom results in a conversion of —CH$_2$— to —C(=O)—. An oxo group that is a substituent of an aromatic carbon atom results in a conversion of —CH— to —C(=O)— and a loss of aromaticity.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups, having 1 to about 8 carbon atoms, or 1 to about 6 carbon atoms); alkenyl and alkynyl groups (including groups having one or more unsaturated linkages and from 2 to about 8, or 2 to about 6 carbon atoms); alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "vinyl" group is a substituent of the formula .HC=.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier, excipient, or diluent. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions of the invention refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Prodrug" means any compound that becomes compound of the invention when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of the invention.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I and at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula I and at least one additional active agent to a patient having or susceptible to a hepatitis C infection.

A "therapeutically effective amount" of a pharmaceutical combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the the limit of quantitation (30 IU/mL, as measured by the Roche TaqMan® assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where $p<0.05$.

Chemical Description

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $R_1$-$R_9$, $R_{16}$, $R_{18}$, $R_{19}$, n, M, Y, and Z. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

In addition to compounds of Formula I as described above, the invention also includes compounds of Formula I in which one or more of the following conditions is met for the variables $R_1$-$R_9$, $R_{16}$, $R_{18}$, $R_{19}$, n, M, Y, and Z. The invention includes compounds of Formula I that carry any combination of the variable definitions set forth below that results in a stable compound.

(Formula I)

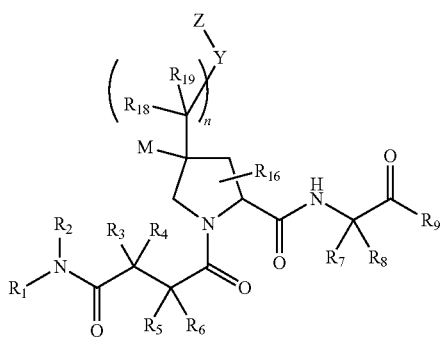

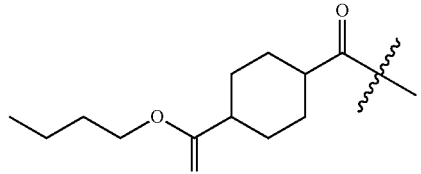

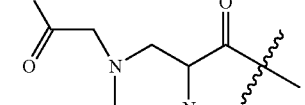

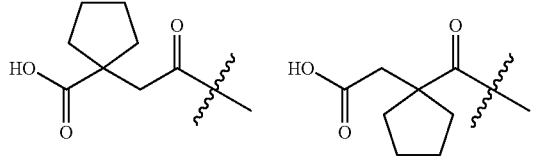

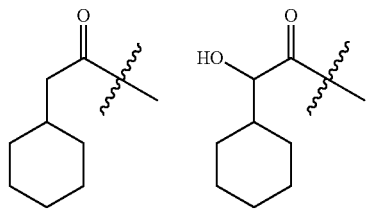

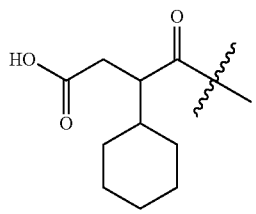

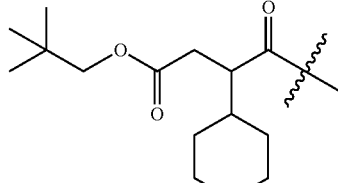

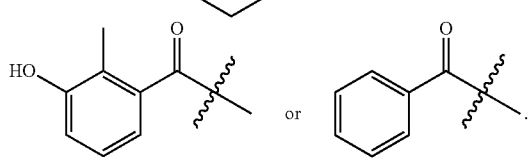

The $R_1$ and $R_2$ Variables

In certain embodiments the variables $R_1$ and $R_2$ carry one of the definitions set forth below.

(1) (2) $R_1$ and $R_2$ are joined to form a 5- to 7-membered heterocyloalkyl ring containing 1 or 2 heteroatoms independently chosen from N, O, and which ring is optionally fused to a 5- or 6-membered heteroaryl group (e. g. phenyl or pyridyl) to form a bicyclic ring system, each of which 5- to 7-membered heterocycloalkyl ring is optionally substituted.

(2) $R_1$ and $R_2$ are joined to form a pyrrolidine, piperidine, or piperazine ring or a piperazine ring fused to a phenyl, each of which is optionally substituted with 0 to 3 substituents independently chosen from A- and AB- where A is halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- or di-$C_1$-$C_4$alkylamino, $C_1$-$C_4$alkylester, $C_1$-$C_4$alkylesteramine, mono- or di-C-$C_4$alkylcarboxamide, $C_1$-$C_2$haloalkyl, or $C_1$-$C_2$haloalkoxy; and B is $C_1$-$C_4$alkyl.

(2) $R_1$ and $R_2$ are joined to form a pyrrolidine, piperidine, or piperazine ring or a piperazine ring fused to a phenyl, each of which is optionally substituted with 0 to 2 substituents independently chosen from halogen, hydroxyl, amino, $CONH_2$, —COOH, $C_1$-$C_2$alkyl, and $C_1$-$C_2$alkoxy.

(3) $R_1$ is $C_1$-$C_4O(C=O)$—, $C_1$-$C_4(C=O)$—

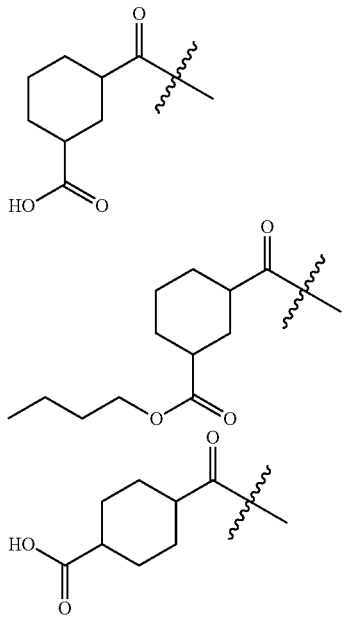

(4) $R_2$ is $C_1$-$C_6$alkyl or $C_3$-$C_7$cycloalkyl.
(5) $R_2$ is hydrogen.

The Variables $R_3$ to $R_8$

In certain embodiments the variables $R_3$ to $R_8$ carry one of the definitions set forth below.

(1) $R_3$, $R_4$, $R_5$, $R_6$, $R_7$, and $R_8$ are independently (a) hydrogen, or (b) $C_1$-$C_4$alkyl or ($C_3$-$C_7$cycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

(2) $R_3$, $R_4$, $R_5$, $R_6$, $R_7$, and $R_8$ are independently hydrogen, $C_1$-$C_4$alkyl, or ($C_3$-$C_7$cycloalkyl)$C_0$-$C_4$alkyl.

(3) $R_3$, $R_4$, $R_5$, $R_6$, $R_7$, and $R_8$ are independently hydrogen or methyl.

(4) Any of $R_3$ and $R_4$ and/or $R_5$ and $R_6$, and/or $R_7$ and $R_8$ are joined to form a 3- to 7-membered cycloalkyl ring or 3- to 7-membered heterocycloalkyl ring containing 1 or 2 heteroatoms independently chosen from N, S, and O, each of which ring is substituted with 0 to 2 substituents independently chosen from halogen, hydroxyl, amino, cyano, vinyl, $C_1$-$C_2$alkyl, $C_1$-$C_2$alkoxy, trifluoromethyl, and trifluoromethoxy.

(5) Any of $R_3$ and $R_4$ and/or $R_5$ and $R_6$, and/or $R_7$ and $R_8$ are joined to form a 3- to 7-membered cycloalkyl ring or 5- to 6-membered heterocycloalkyl ring containing 1 or 2 heteroatoms independently chosen from N, S, and O, each of which ring is substituted with 0 to 2 substituents independently chosen from halogen, hydroxyl, $C_1$-$C_2$alkyl, and $C_1$-$C_2$alkoxy.

(6) $R_3$, $R_4$, and $R_6$, are independently hydrogen or methyl;

$R_5$ is $C_1$-$C_6$alkyl, $C_2$-$C_6$alkenyl, ($C_3$-$C_7$cycloalkyl)$C_0$-$C_4$alkyl, ($C_3$-$C_7$cycloalkenyl)$C_0$-$C_4$alkyl, (heterocycloalkyl)$C_0$-$C_4$alkyl, $C_2$-$C_6$alkanoyl, or mono- or di-$C_1$-$C_6$alkylamino; and $R_7$ and $R_8$ are joined to form an optionally substituted 3- to 7-membered cycloalkyl ring or an optionally substituted 3- to 7-membered heterocycloalkyl ring containing 1 or 2 heteroatoms independently chosen from N, S, and O.

(7) $R_5$ is $C_1$-$C_6$alkyl or ($C_3$-$C_7$cycloalkyl)$C_0$-$C_4$alkyl; and $R_7$ and $R_8$ are joined to form a cyclopropyl ring, which is unsubstituted or substituted with 1 or 2 $C_1$-$C_6$alkyl or $C_2$-$C_6$alkenyl.

(8) The invention includes compounds in which $R_3$ and $R_4$ are hydrogen, $R_5$ is hydrogen, $R_6$ is t-butyl, and $R_7$ and $R_8$ are joined to form a cyclopropyl group substituted by a vinyl group. For example the invention includes compounds of Formula II

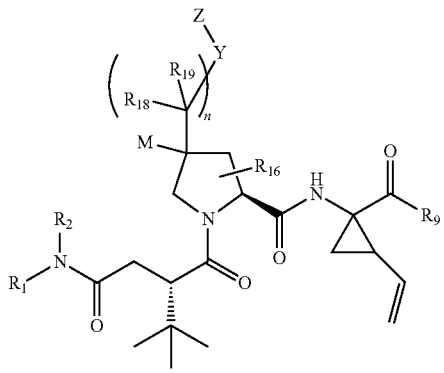
(Formula II)

(9) $R_3$, $R_4$, $R_6$, and $R_8$ are independently hydrogen or methyl; and $R_5$ is a $C_7$-$C_{11}$ saturated or unsaturated hydrocarbon chain that is covalently bound to $R_7$, where $R_7$ is a methylene group. For example the invention includes compound of Formula III

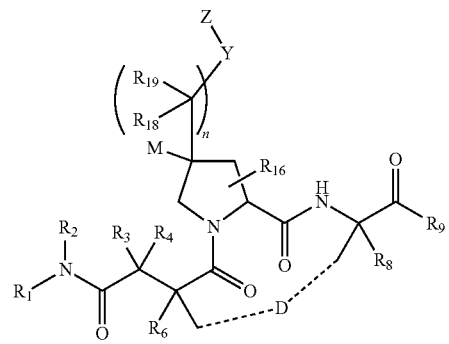
(Formula III)

where D is an alkyl or alkenyl group having 6 to 10 carbon atoms.

(10) The invention also includes compounds in which $R_3$ and $R_4$ are both hydrogen, and $R_5$ is covalently bound to $R_7$ via an 8-membered mono-unsaturated hydrocarbon chain. For Example in the invention includes compounds of Formula (IV)

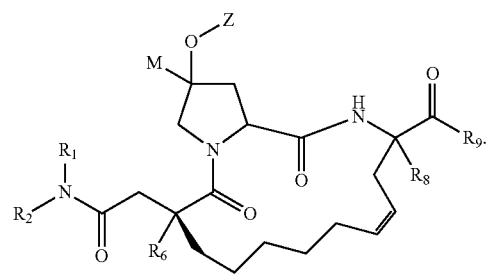
(Formula IV)

(11) $R_3$, $R_4$, and $R_6$ are independently hydrogen or methyl; and $R_5$ is a $C_7$-$C_{11}$ saturated or unsaturated hydrocarbon chain that is covalently bound to an optionally substituted cycloalkyl ring formed by $R_7$ and $R_8$ being joined to from a 3- to 7-membered optionally substituted cycloalkyl ring. For example the invention includes compounds and salts of Formula V

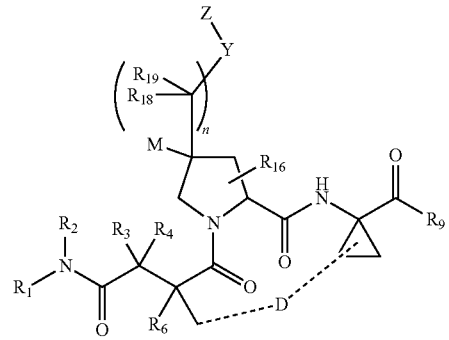
(Formula V)

where D is an alkyl or alkenyl group having 6 to 10 carbon atoms.

(12) The invention also includes compounds and salts in which $R_3$ and $R_4$ are both hydrogen and $R_5$ is a 7-carbon mono-unsaturated hydrocarbon chain that is covalently bound to a substituted cycloalkyl ring formed by $R_7$ and $R_8$. For example the invention includes compounds and salts of Formula VI and VI-A:

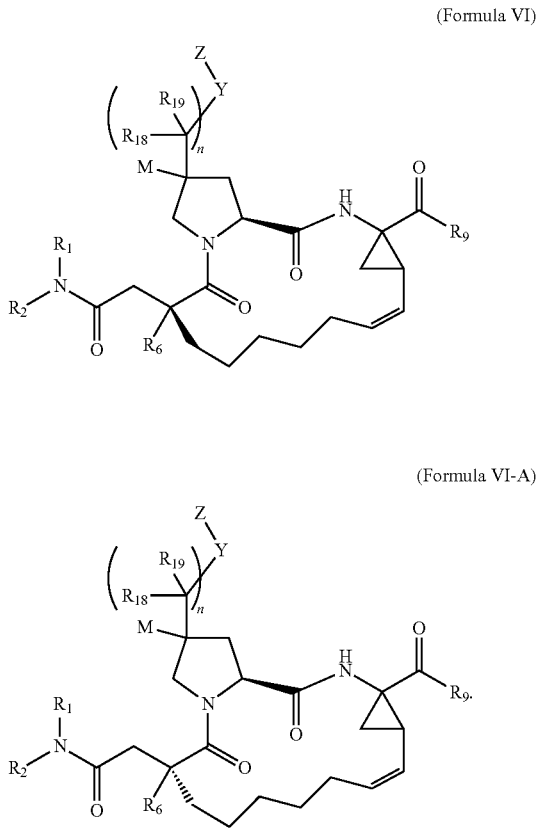

(Formula VI)

(Formula VI-A)

The $R_9$ Variable

In certain embodiments the $R_9$ variable carries one of the definitions set forth below.

(1) T is a group of the formula

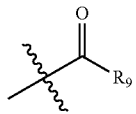

and $R_9$ is hydroxyl, amino, —COOH, —$NR_{10}R_{11}$, —$OR_{12}$, —$SR_{12}$, —$NR_{10}(S=O)R_{11}$, —$NR_{10}SO_2R_{11}$, —$NR_{10}SONR_{11}R_{12}$, —$NR_{10}SO_2NR_{11}R_{12}$, —(C=O)$OR_{10}$, —$NR_{10}(C=O)OR_{11}$, or —$CONR_{10}R_{11}$.

(2) $R_9$ is hydroxyl, amino, —COOH, —$NR_{10}R_{11}$, —$OR_{12}$, —$NR_{10}SO_2R_{11}$, —(C=O)$OR_{10}$, or —$CONR_{10}R_{11}$.

(3) $R_9$ is $C_1$-$C_6$alkyl, $C_2$-$C_6$alkenyl, $C_2$-$C_6$alkanoyl, ($C_3$-$C_7$cycloalkyl)$C_0$-$C_4$alkyl, ($C_3$-$C_7$cycloalkenyl)$C_0$-$C_4$alkyl, (heterocycloalkyl)$C_0$-$C_4$alkyl, (aryl)$C_0$-$C_2$alkyl, or (5- to 10-membered heteroaryl)$C_0$-$C_2$alkyl, each of which is substituted with 0 or 1 or more substituents independently chosen from halogen, hydroxyl, amino, cyano, oxo —COOH, —$CONH_2$, oxo, $C_1$-$C_4$alkyl, $C_1$-$C_4$alkoxy, $C_2$-$C_4$alkanoyl, $C_1$-$C_4$alkylthio, mono- and di-$C_1$-$C_4$alkylamino, $C_1$-$C_4$alkylester, mono- and di-$C_1$-$C_4$alkylcarboxamide, $C_1$-$C_2$haloalkyl, and $C_1$-$C_2$haloalkoxy.

(4) $R_9$ is $C_1$-$C_6$alkyl, $C_2$-$C_6$alkenyl, $C_2$-$C_6$alkanoyl, ($C_3$-$C_7$cycloalkyl)$C_0$-$C_4$alkyl, ($C_3$-$C_7$cycloalkenyl)$C_0$-$C_4$alkyl, (heterocycloalkyl)$C_0$-$C_4$alkyl, (aryl)$C_0$-$C_2$alkyl, or (5- to 10-membered heteroaryl)$C_0$-$C_2$alkyl each of which is substituted with 0 or 1 or more substituents independently chosen from halogen, hydroxyl, amino, cyano, oxo —COOH, —$CONH_2$, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

(5) $R_9$ is a phosphonate of the formula

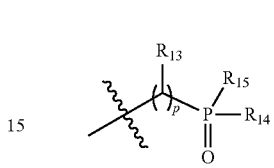

where p is 1 or 2 and $R_{13}$-$R_{15}$ carry the values set forth in the "Summary of the Invention" section.

(6) $R_9$ is $R_XXC_1$-$C_4$alkyl-, where X is —(C=O)NH—, —NH(C=O)— and $R_X$ is phenyl or pyridyl.

(7) $R_9$ is —CH($R_Y$)($C_3$-$C_7$cycloalkyl), —$SO_2CH(R_Y)$($C_3$-$C_7$cycloalkyl), or —$NR_{10}SO_2CH(R_Y)$($C_3$-$C_7$cycloalkyl), where $R_Y$ is halogen, or $R_Y$ is $C_1$-$C_2$alkyl, $C_2$-$C_6$alkanoyl, ($C_3$-$C_7$cycloalkyl)$C_0$-$C_2$alkyl, (phenyl)$C_0$-$C_4$alkyl, (phenyl)$C_0$-$C_4$alkoxy, (heterocycloalkyl)$C_0$-$C_2$alkyl, or (5- to 10-membered heteroaryl)$C_0$-$C_4$alkyl, each of which is substituted with 0 or 1 or more substituents independently chosen from halogen, hydroxyl, amino, cyano, oxo —COOH, —$CONH_2$, oxo, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

(8) $R_9$ is —$NR_{10}SO_2R_{11}$. In some embodiments $R_{10}$ is hydrogen or methyl and $R_{11}$ is cyclopropyl.

The $R_{10}$, $R_{11}$, and $R_{12}$ Variables

In any of the above definitions of $R_9$ the variables $R_{10}$, $R_{11}$, and $R_{12}$ may carry the definition set forth for Formula I in the "Summary of the Invention" section. $R_{10}$, $R_{11}$, and $R_{12}$ may also carry any of definitions that follow.

(1) $R_{10}$, $R_{11}$, and $R_{12}$ are independently $C_1$-$C_6$alkyl, $C_2$-$C_6$alkenyl, $C_2$-$C_6$alkynyl, ($C_3$-$C_7$cycloalkyl)$C_0$-$C_4$alkyl, (heterocycloalkyl)$C_0$-$C_4$alkyl, (phenyl)$C_0$-$C_2$alkyl, (naphthyl)$C_0$-$C_2$alkyl, or (5- to 10-membered heteroaryl)$C_0$-$C_2$alkyl, each of which is substituted with 0 to 3 substituents independently chosen from halogen, hydroxyl, amino, cyano, oxo —COOH, —$CONH_2$, oxo, $C_1$-$C_4$alkyl, $C_1$-$C_4$alkoxy, $C_2$-$C_4$alkanoyl, $C_1$-$C_4$alkylthio, mono- and di-$C_1$-$C_4$alkylamino, $C_1$-$C_4$alkylester, mono- and di-$C_1$-$C_4$alkylcarboxamide, $C_1$-$C_2$haloalkyl, and $C_1$-$C_2$haloalkoxy.

(2) $R_{10}$, $R_{11}$, and $R_{12}$ are independently hydrogen, or $C_1$-$C_6$alkyl, $C_2$-$C_6$alkenyl, $C_2$-$C_6$alkynyl, ($C_3$-$C_7$cycloalkyl)$C_0$-$C_2$alkyl, (heterocycloalkyl)$C_0$-$C_2$alkyl, (phenyl)$C_0$-$C_2$alkyl, or (5- to 6-membered monocyclic heteroaryl)$C_0$-$C_2$alkyl, each of which is substituted with 0 to 3 substituents independently chosen from halogen, hydroxyl, oxo, $C_1$-$C_2$alkyl, $C_1$-$C_2$alkoxy, trifluoromethyl, and trifluoromethoxy.

(3) $R_{10}$, $R_{11}$, and $R_{12}$ are independently hydrogen or $C_1$-$C_6$alkyl.

The Y, M, J, L, and Z Variables

The invention includes compounds and salts of Formulae I to VI in which Y, M, and Z carry the variables set forth below. Y, M, and Z include the variables n, $R_{18}$, and $R_{19}$.

(1) Y is absent, $CH_2$, O, or —O(C=O)— and n is 0.

(2) Y is O and n is 0.

(3) Y is absent, $CH_2$, O, or —O(C=O)—, and $R_{18}$ and $R_{19}$ are independently hydrogen or methyl, and n is 1.
(4) The invention includes compounds and salts in which n is 1.
(5) M is hydrogen.
(6) J and L are both $CH_2$.
(7) Z is 1-naphthyl, 2-napthyl,
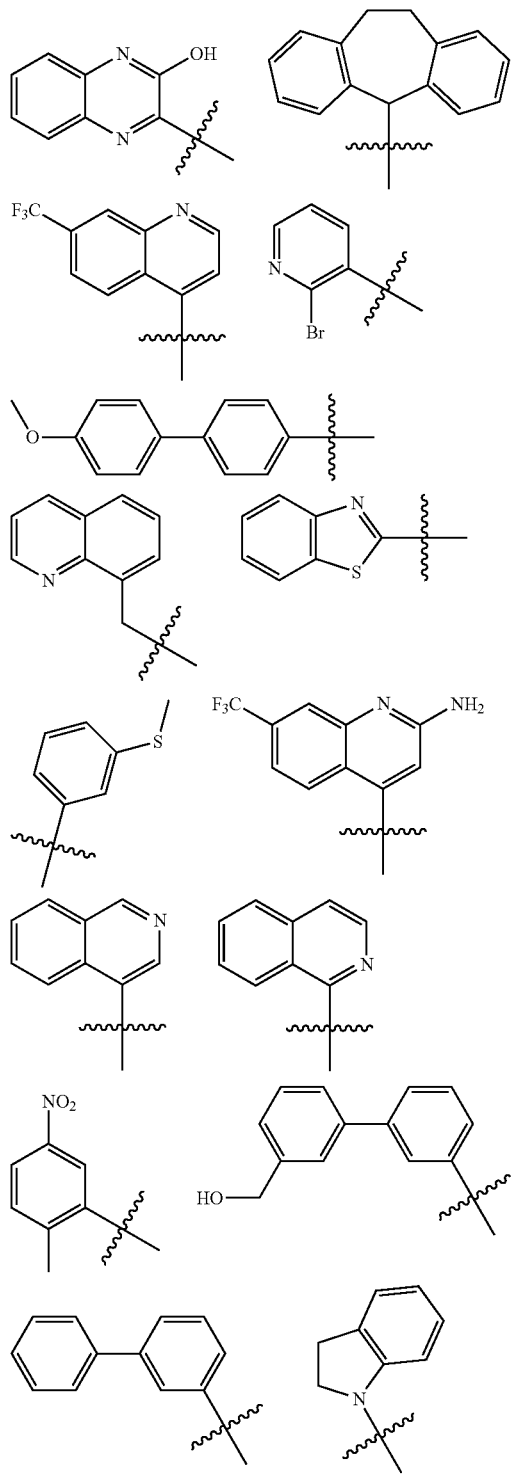
-continued
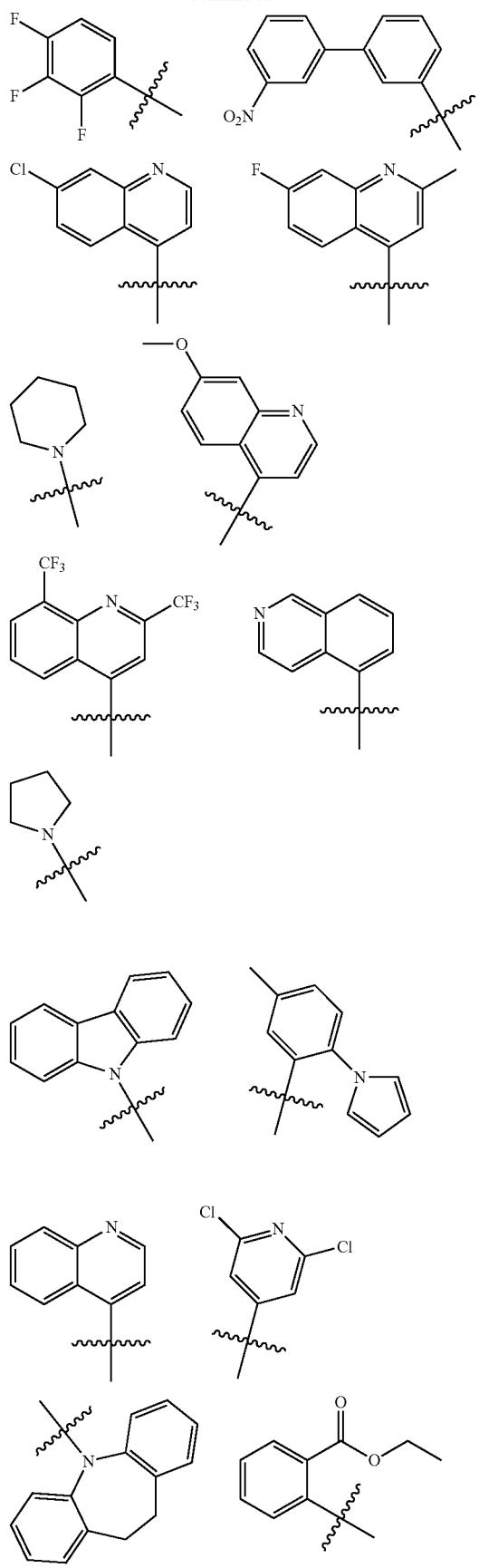

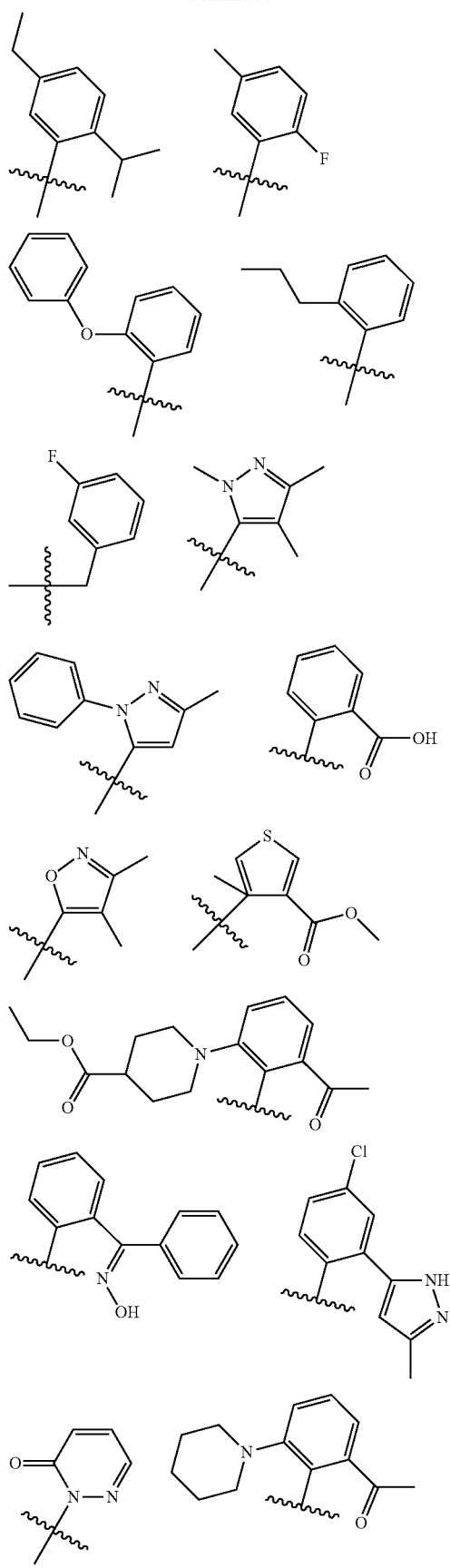
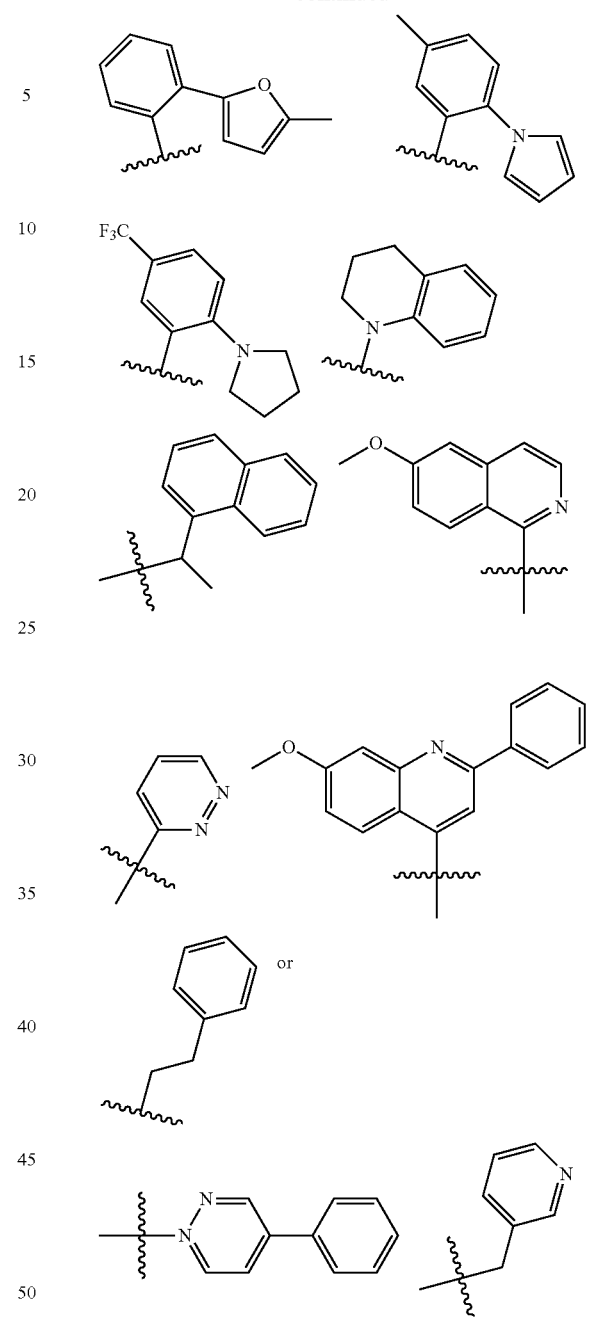
(8) Z is a group of the formula
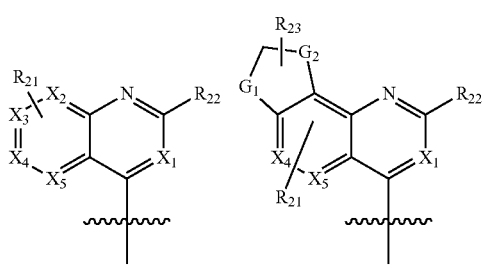

-continued

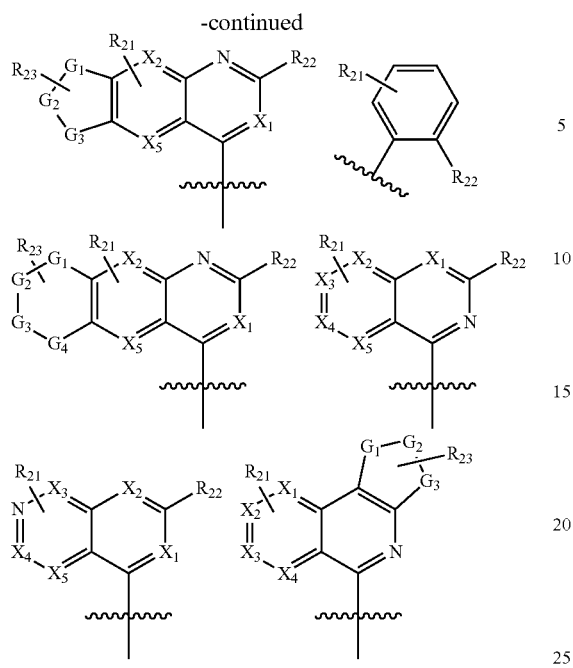

Within the above chemical formula $X_1$-$X_5$, $G_1$-$G_4$, and $R_{21}$-$R_{24}$ carry the following definitions.

$X_1$, $X_2$, $X_3$, $X_4$, and $X_5$ are independently N or CH and no more than two of $X_1$-$X_5$ are N.

$G_1$, $G_2$, $G_3$, and $G_4$ are independently $CH_2$, O, S, or $NR_{24}$, wherein no more than two of $G_1$ to $G_4$ are other than hydrogen.

$R_{21}$ represents from 0 to 3 groups independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_{22}$ is hydrogen, halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, or $R_{22}$ is ($C_3$-$C_7$cycloalkyl)$C_0$-$C_2$alkyl, (phenyl)$C_0$-$C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, naphthyl, indanyl, (5- or 6-membered heterocycloalkyl)$C_0$-$C_2$alkyl, or 9- or 10 membered bicyclic heteroaryl, each of which is substituted with 0, 1, or 2 substituents independently chosen from (c) halogen, hydroxyl, amino, cyano, nitro, —COOH, —$CONH_2$, $CH_3$(C=O)NH—, $C_1$-$C_4$alkyl, $C_1$-$C_4$alkoxy, $C_1$-$C_4$hydroxyalkyl, mono- and di-$C_1$-$C_4$alkylamino, —$NR_8SO_2R_{11}$, —$C(O)OR_{11}$, —$NR_8COR_{11}$, —$NR_8C(O)OR_{11}$, trifluoromethyl, trifluoromethoxy, and (d) phenyl and 5- or 6-membered heteroaryl, each of which is substituted with 0 or 1 or more of halogen, hydroxyl, $C_1$-$C_4$alkyl, $C_1$-$C_2$alkoxy.

$R_{23}$ is 0 to 2 substituents independently chosen from halogen, hydroxyl, $C_1$-$C_2$alkyl, and $C_1$-$C_2$alkoxy.

$R_{24}$ is independently chosen at each occurrence from hydrogen and $C_1$-$C_2$alkyl.

In certain embodiments $R_{22}$ is

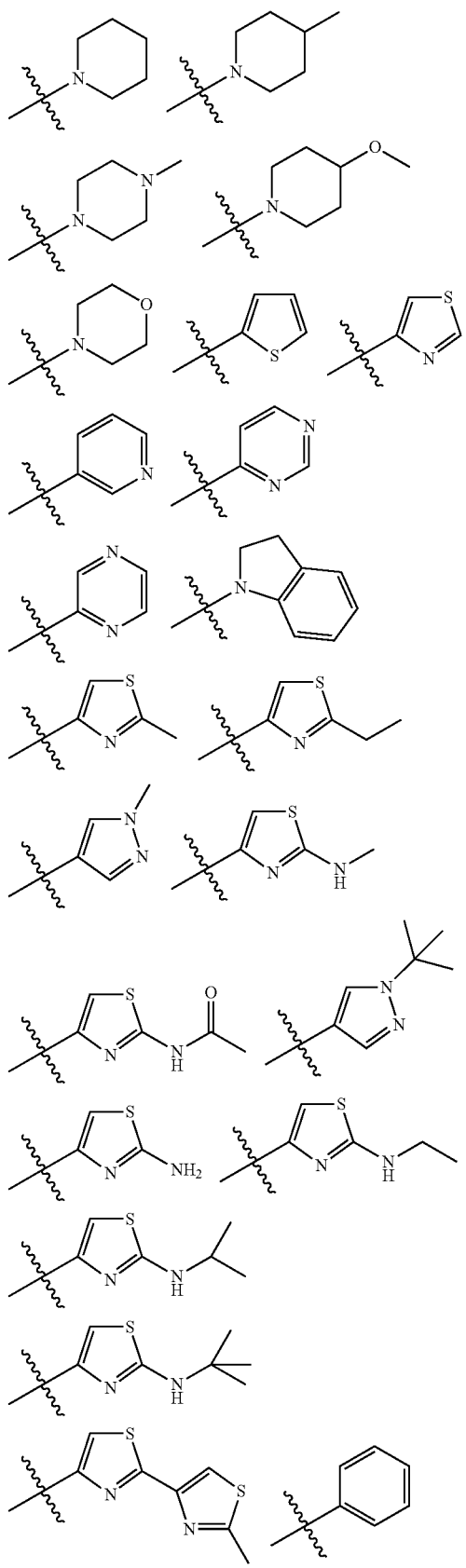

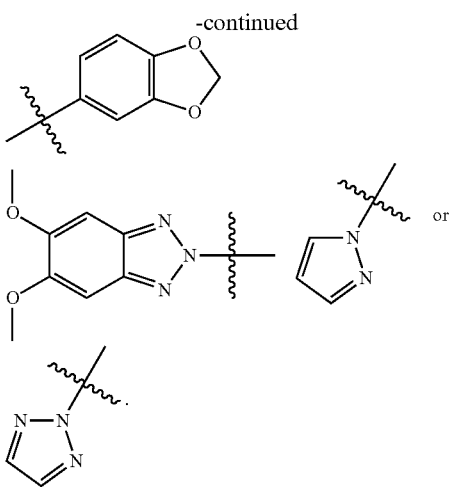

(9) Z is a group of the formula

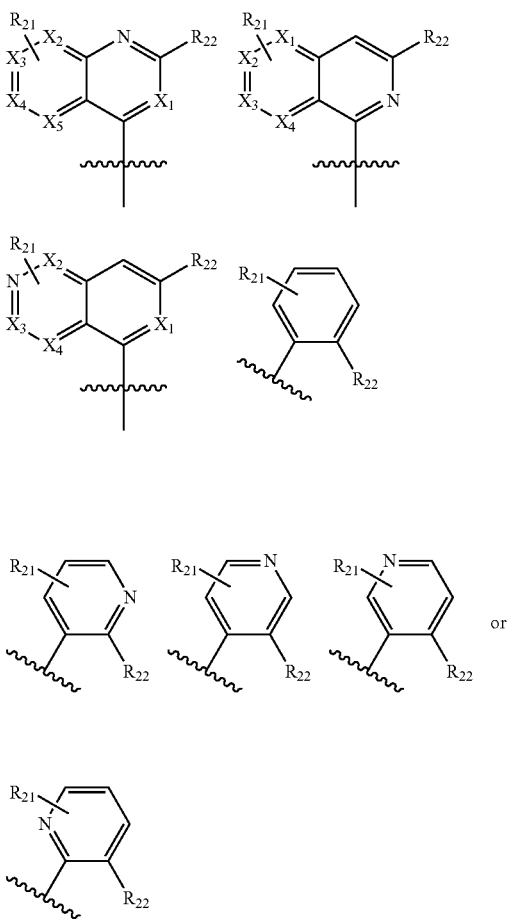

Within this embodiment $X_1$-$X_5$ and $R_{21}$-$R_{23}$ carry the following definitions.

$X_1$, $X_2$, $X_3$, and $X_4$, are independently N or CH and no more than two of $X_1$-$X_4$ are N.

$R_{21}$ represents from 0 to 3 groups independently chosen from halogen, hydroxyl, amino, cyano, —CONH$_2$, —COOH, C$_1$-C$_4$alkyl, C$_2$-C$_4$alkanoyl, C$_1$-C$_4$alkoxy, C$_1$-C$_4$alkylthio, mono- and di-C$_1$-C$_4$alkylamino, C$_1$-C$_2$haloalkyl, and C$_1$-C$_2$haloalkoxy.

$R_{22}$ is hydrogen, halogen, hydroxyl, amino, cyano, —CONH$_2$, —COOH, C$_1$-C$_4$alkyl, C$_2$-C$_4$alkanoyl, C$_1$-C$_4$alkoxy, C$_1$-C$_4$alkylthio, mono- and di-C$_1$-C$_4$alkylamino, C$_1$-C$_4$alkylester, C$_1$-C$_2$haloalkyl, and C$_1$-C$_2$haloalkoxy.

Or, $R_{22}$ is (C$_3$-C$_7$cycloalkyl)C$_0$C$_2$alkyl, (phenyl)C$_0$-C$_2$alkyl, (phenyl)C$_0$-C$_2$alkoxy, (5- or 6-membered heteroaryl)C$_0$-C$_2$alkyl, (5- or 6-membered heteroaryl)C$_0$-C$_2$alkoxy, naphthyl, indanyl, (5- or 6-membered heterocycloalkyl)C$_0$C$_2$alkyl, or 9- or 10 membered bicyclic heteroaryl, each of which is substituted with 0, 1, or 2 substituents independently chosen from (c) halogen, hydroxyl, amino, cyano, nitro, —COOH, —CONH$_2$, CH$_3$(C=O)NH—, C$_1$-C$_4$alkyl, C$_1$-C$_4$alkoxy, C$_1$-C$_4$hydroxyalkyl, mono- and di-C$_1$-C$_4$alkylamino, —NR$_8$SO$_2$R$_{11}$, —C(O)OR$_{11}$, —NR$_8$COR$_{11}$, —NR$_8$C(O)OR$_{11}$, trifluoromethyl, and trifluoromethoxy, and (d) phenyl and 5- or 6-membered heteroaryl, each of which is substituted with 0 or 1 or more of halogen, hydroxyl, C$_1$-C$_4$alkyl, C$_1$-C$_2$alkoxy.

(10) Z is a group of the formula

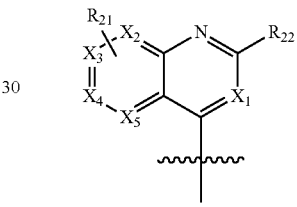

wherein $X_1$-$X_5$ and $R_{21}$-$R_{22}$ carry the definitions set forth for embodiment (7), immediately above.

(9) Z is a quinoline of the formula

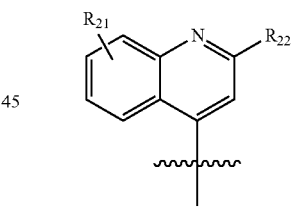

wherein $X_1$-$X_5$ and $R_{21}$-$R_{22}$ carry the definitions set forth for embodiment (7).

Or in certain embodiments, $R_{21}$ represents a substituent at the 7-position of the quinoline, and 0 to 2 additional substituents independently chosen from halogen, hydroxyl, amino, cyano, —CONH$_2$, —COOH, C$_1$-C$_4$alkyl, C$_2$-C$_4$alkanoyl, C$_1$-C$_4$alkoxy, mono- and di-C$_1$-C$_4$alkylamino, C$_1$-C$_2$haloalkyl, and C$_1$-C$_2$haloalkoxy, and $R_{22}$ is (phenyl)C$_0$-C$_2$alkyl or (pyridyl)C$_0$-C$_2$alkyl, each of which is substituted with 0, 1, or 2 substituents independently chosen from halogen, hydroxyl, amino, cyano, —COOH, —CONH$_2$, C$_1$-C$_4$alkyl, C$_1$-C$_4$alkoxy, mono- and di-C$_1$-C$_4$alkylamino, trifluoromethyl, and trifluoromethoxy.

(10) The invention includes compounds and salts wherein n is 0, Z is absent, and Y and M are taken together to form a ring, so that

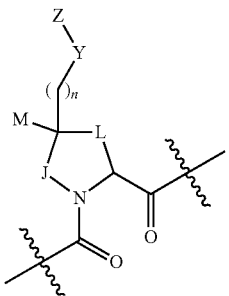

is a group for the formula:

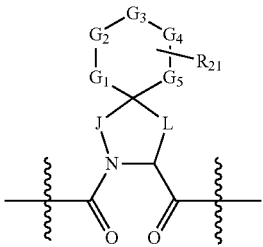

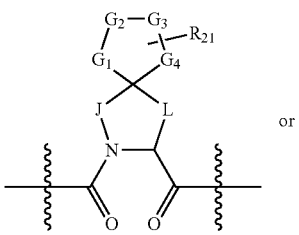

or

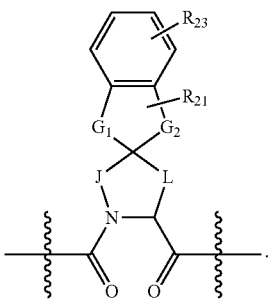

Within this embodiment $G_1$, $G_2$, $G_3$, $G_4$, and $G_5$ are independently $CH_2$, O, S, or $NR_{22}$; wherein no more than two of $G_1$, $G_2$, $G_3$, $G_4$, and $G_5$ are other than $CH_2$.

$R_{21}$ is 0 to 2 substituents independently chosen from halogen, hydroxy, $C_1$-$C_2$alkyl, and $C_1$-$C_2$alkoxy;

$R_{22}$ is independently chosen at each occurrence from hydrogen and methyl; and $R_{23}$ is 0 to 2 substituents independently chosen from halogen, hydroxy, $C_1$-$C_2$alkyl, and $C_1$-$C_2$alkoxy.

(11) The invention includes compounds and salts in which n is 0, M is hydrogen, Z is absent, and Y and J are taken together to form a ring, so that

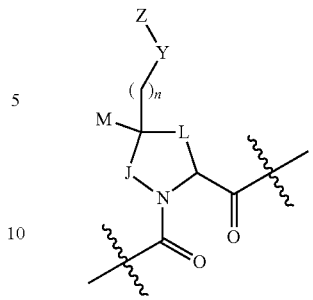

is a group for the formula:

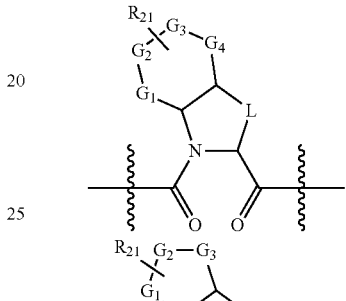

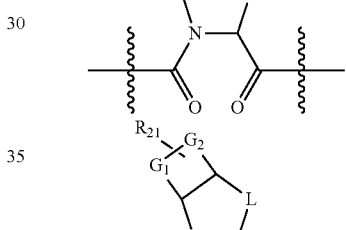

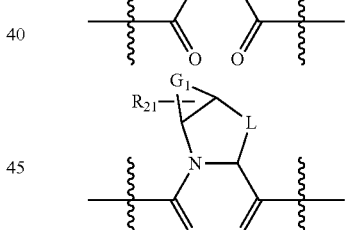

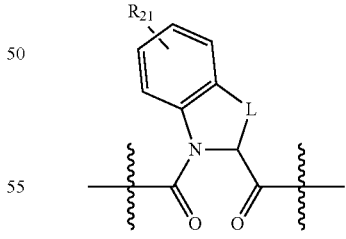

or

Within this embodiment $G_1$, $G_2$, $G_3$, and $G_4$ are independently $CH_2$, O, S, or $NR_{22}$; wherein no more than two of $G_1$, $G_2$, $G_3$, and $G_4$ are other than $CH_2$.

$R_{21}$ is 0 to 2 substituents independently chosen from halogen, hydroxy, $C_1$-$C_2$alkyl, and $C_1$-$C_2$alkoxy;

$R_{22}$ is 0 to 2 substituents independently chosen from halogen, hydroxy, $C_1$-$C_2$alkyl, and $C_1$-$C_2$alkoxy; and $R_{23}$ is 0 to 2 substituents independently chosen from halogen, hydroxy, $C_1$-$C_2$alkyl, and $C_1$-$C_2$alkoxy.

(12) The invention further includes compounds and salts of wherein
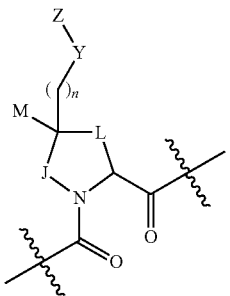
is a group for the formula:
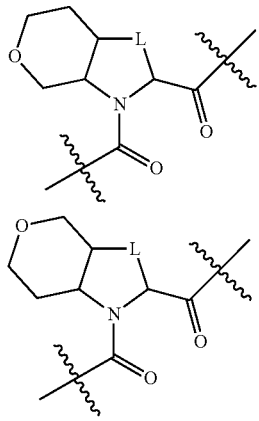
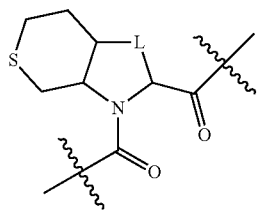
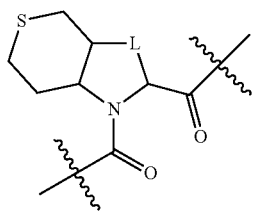
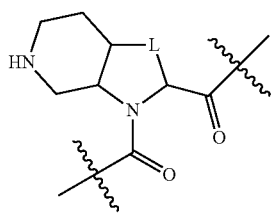
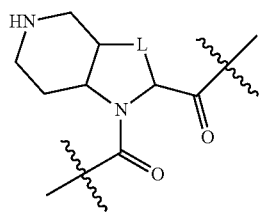
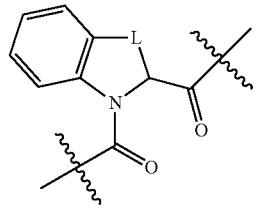
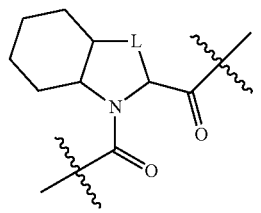
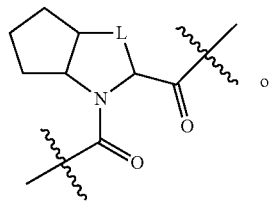 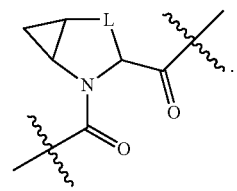 or
(13) The invention includes compounds and n is 0, Z is absent, and Y and L are taken together to form a ring, so that
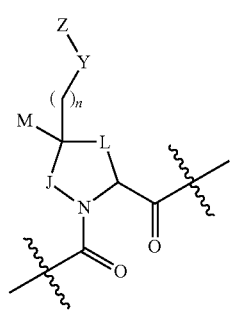
is a group for the formula:
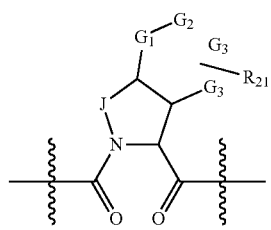

33

-continued

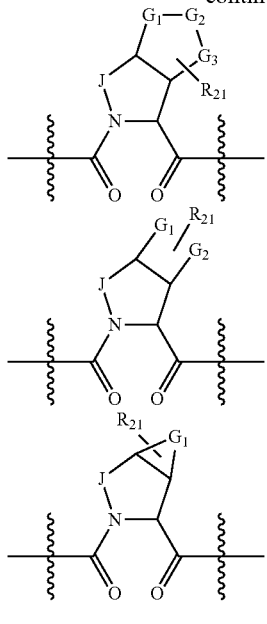

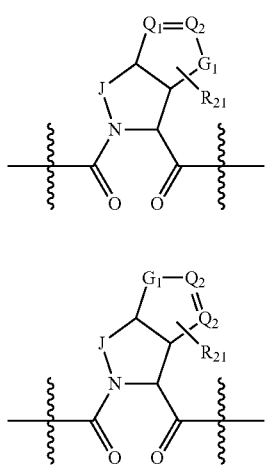

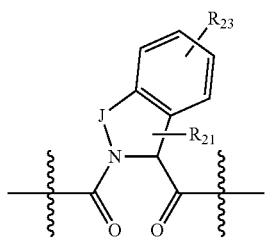

or

Within this embodiment $G_1$, $G_2$, $G_3$, and $G_4$ are independently $CH_2$, O, S, or $NR_{22}$; wherein no more than two of $G_1$, $G_2$, $G_3$, and $G_4$ are other than $CH_2$.

$Q_1$ and $Q_2$ are independently CH or N.

$R_{21}$ is 0 to 2 substituents independently chosen from halogen, hydroxy, $C_1$-$C_2$alkyl, and $C_1$-$C_2$alkoxy;

$R_{22}$ is 0 to 2 substituents independently chosen from halogen, hydroxy, $C_1$-$C_2$alkyl, and $C_1$-$C_2$alkoxy; and $R_{23}$ is 0 to 2 substituents independently chosen from halogen, hydroxy, $C_1$-$C_2$alkyl, and $C_1$-$C_2$alkoxy.

34

(14) The invention includes compounds and salts wherein

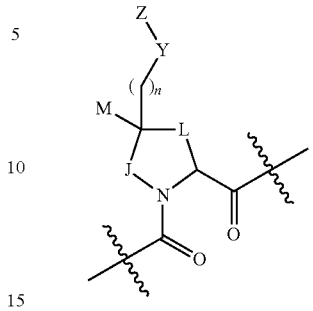

is a group for the formula:

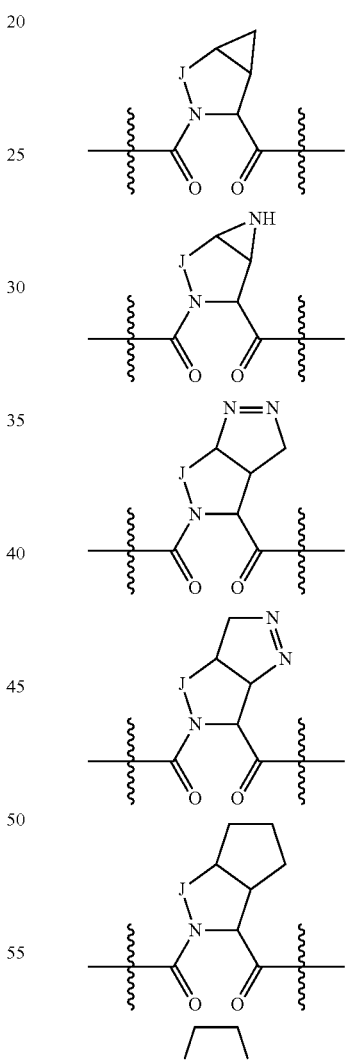

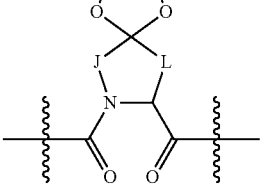

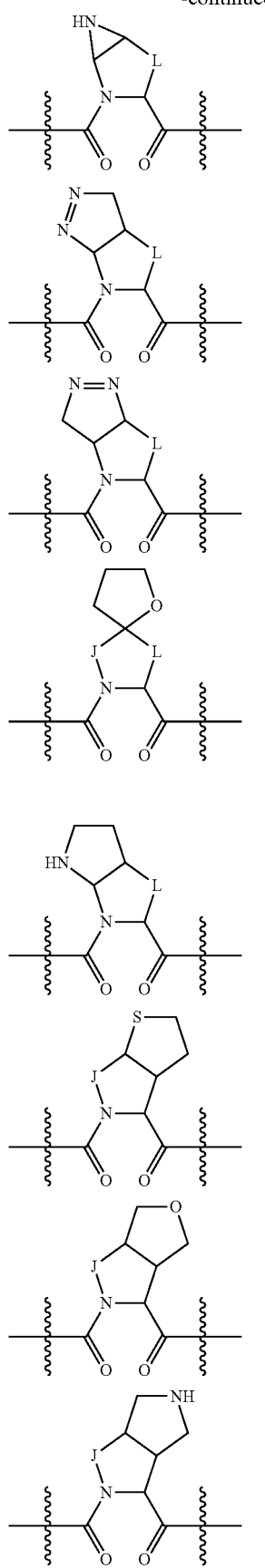
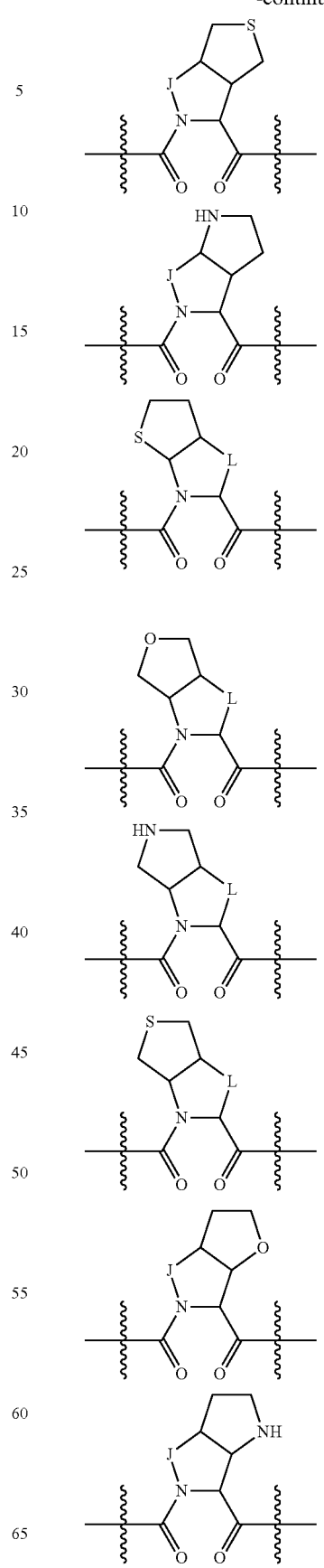

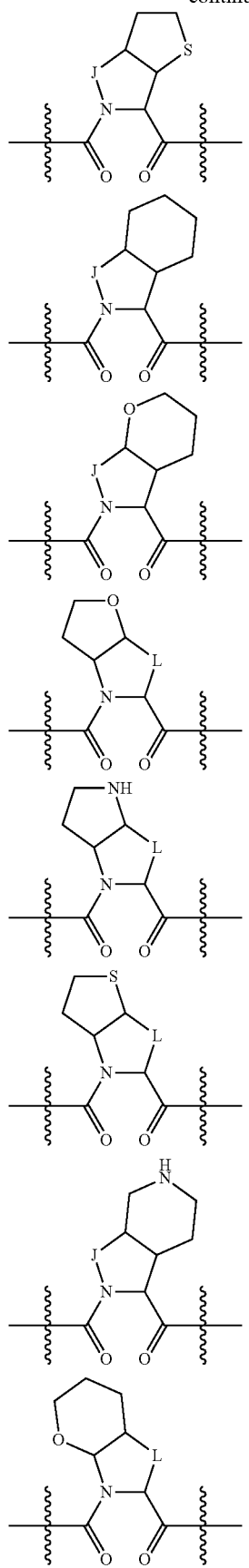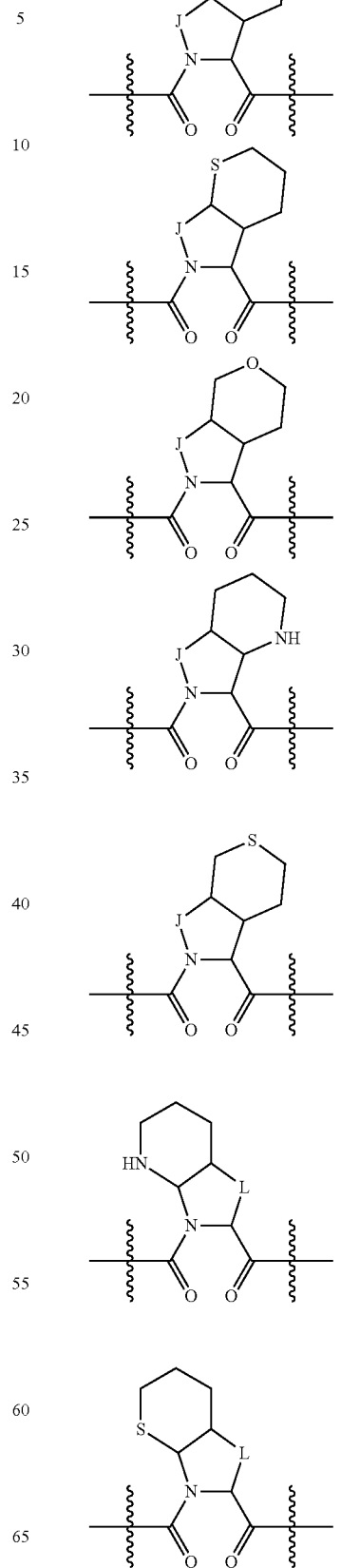

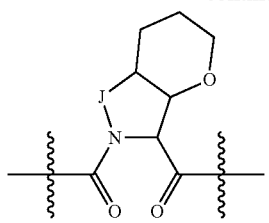
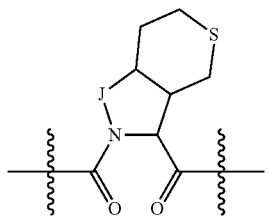
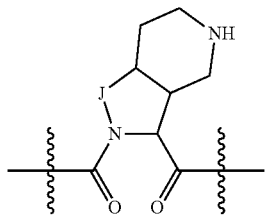
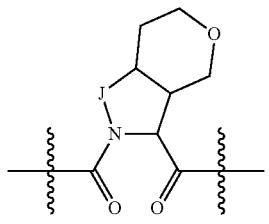
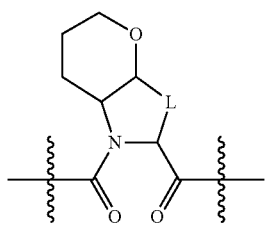
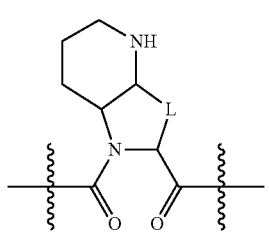
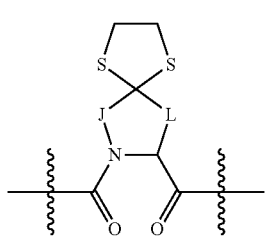
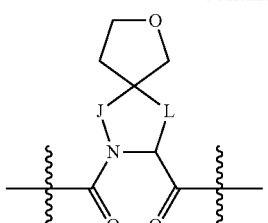
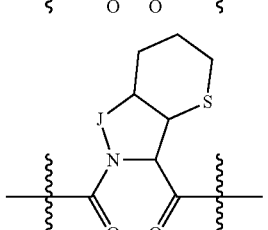
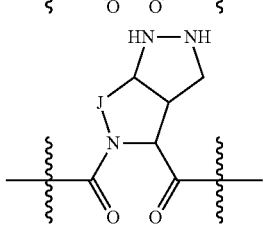
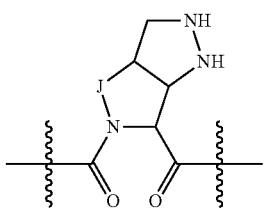
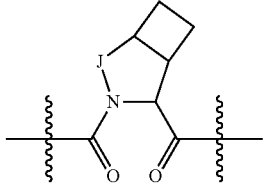
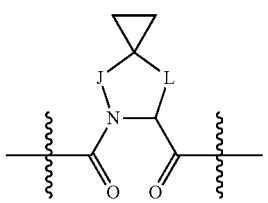
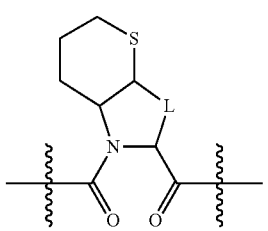
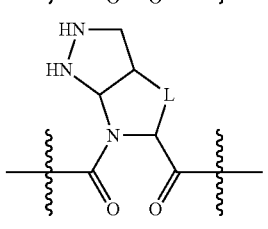

-continued

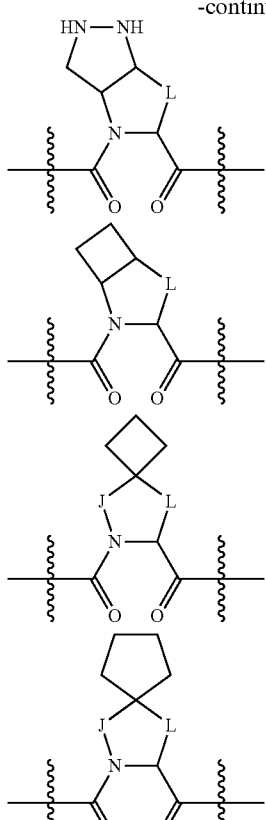

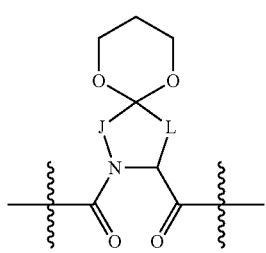

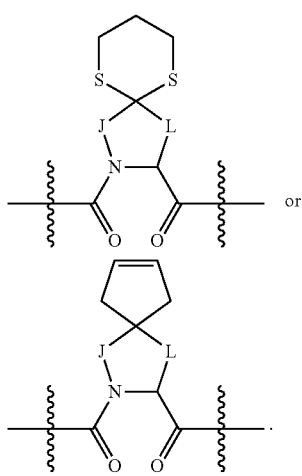

(15) The invention includes compounds and salts of Formula VII and Formula VIII in which Y is oxygen.

Formula VII

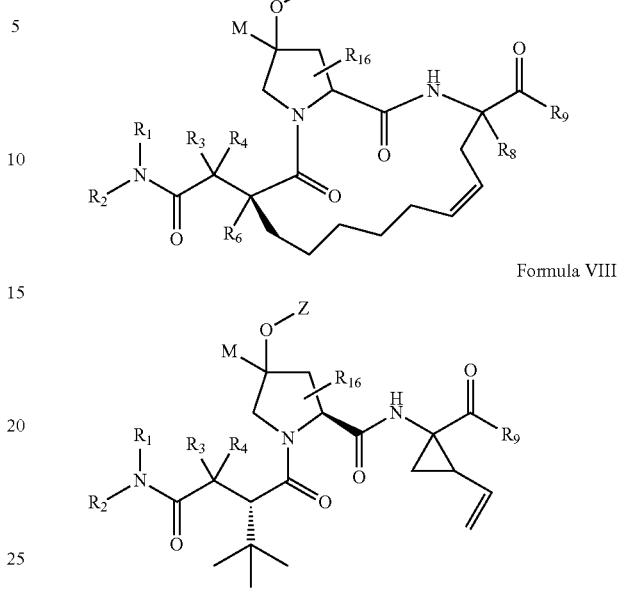

Formula VIII

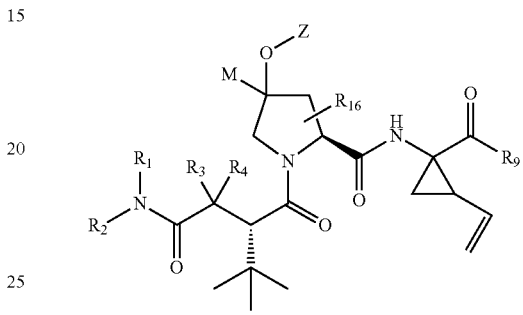

Within this embodiment:

$R_1$ and $R_2$ are joined to form a pyrrolidine, piperidine, or piperazine ring or a piperazine ring fused to a phenyl, each of which is optionally substituted with 0 to 2 substituents independently chosen from halogen, hydroxyl, amino, $CONH_2$, —COOH, $C_1$-$C_2$alkyl, and $C_1$-$C_2$alkoxy.

$R_3$, $R_4$, $R_6$, and $R_8$ are independently chosen from hydrogen, $C_1$-$C_4$alkyl, and ($C_3$-$C_7$cycloalkyl)$C_0$-$C_2$alkyl.

$R_9$ is hydroxyl, amino, —COOH, —$NR_{10}R_{11}$, —$OR_{12}$, —$NR_{10}SO_2R_{11}$, —(C=O)$OR_{10}$, or —$CONR_{10}R_{11}$.

$R_{10}$, $R_{11}$, and $R_{12}$ are independently hydrogen, or $C_1$-$C_6$alkyl, $C_2$-$C_6$alkenyl, $C_2$-$C_6$alkynyl, ($C_3$-$C_7$cycloalkyl)$C_0$-$C_2$alkyl, (heterocycloalkyl)$C_0$-$C_2$alkyl, (phenyl)$C_0$-$C_2$alkyl, or (5- to 6-membered monocyclic heteroaryl)$C_0$-$C_2$alkyl, each of which is substituted with 0 to 3 substituents independently chosen from halogen, hydroxyl, oxo, $C_1$-$C_2$alkyl, $C_1$-$C_2$alkoxy, trifluoromethyl, and trifluoromethoxy.

$R_{16}$ is 0 to 2 substituents independently chosen from halogen, $C_1$-$C_2$alkyl, and $C_1$-$C_2$alkoxy.

M is hydrogen or methyl.

(11) Z is a quinoline of the formula

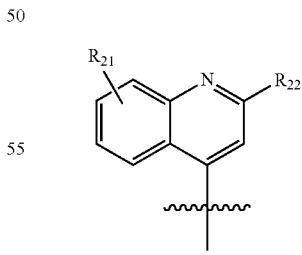

in which, $R_{21}$ represents a substituent at the 7-position of the quinoline, and 0 to 2 additional substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, mono- and di-$C_1$-$C_4$alkylamino, $C_1$-$C_2$haloalkyl, and $C_1$-$C_2$haloalkoxy; and $R_{22}$ is (phenyl)$C_0$-$C_2$alkyl or (pyridyl)$C_0$-$C_2$alkyl, each of which is substituted with 0, 1, or 2 substituents independently chosen from halogen, hydroxyl, amino, cyano, —COOH, —CONH$_2$, $C_1$-$C_4$alkyl, $C_1$-$C_4$alkoxy, mono- and di-$C_1$-$C_4$alkylamino, trifluoromethyl, and trifluoromethoxy.

Pharmaceutical Preparations

Compounds of the invention can be administered as the neat chemical, but are preferably administered as a pharmaceutical composition. Accordingly, the invention provides pharmaceutical formulations comprising a compound or pharmaceutically acceptable salt of the invention, together with at least one pharmaceutically acceptable carrier.

Compounds of the invention may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Binders are substances that bind or "glue" powders together and make them cohesive by forming granules, thus serving as the "adhesive" in the formulation. Binders add cohesive strength to that already available in the diluent or bulking agent. Examples of binders include starch, gelatin, natural sugars, corn sweeteners, natural and synthetic gums such as acacia, sodium alginate, carboxymethylcellulose, polyethylene glycol and waxes. The amount of binder in the composition can range, for example, from about 2 to about 20% by weight of the composition, or from about 3 to about 10% by weight, even more preferably from about 3 to about 6% by weight.

Diluents include sugars such as lactose, sucrose, mannitol and sorbitol; starches derived from wheat, corn, rice and potato; and celluloses such as microcrystalline cellulose. The amount of diluent in the composition may be, for example, about 10 to about 90% by weight of the total composition, about 25 to about 75%, about 30 to about 60% by weight, or about 12 to about 60%.

Disintegrants are materials added to a pharmaceutical composition to help it break apart (disintegrate) and release the active agent. Suitable disintegrants include starches; including "cold water soluble" modified starches such as sodium carboxymethyl starch; natural and synthetic gums such as locust bean, karaya, guar, and tragacanth gum and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range, for example, from about 2 to about 15% by weight of the composition or from about 4 to about 10% by weight.

Lubricants are substances added to a pharmaceutical formulation to enable the tablet, granules, etc. after it has been compressed, to release from the; mold or die by reducing friction or wear. Examples of lubricants useful in pharmaceutical dosage forms include boric acid, sodium benzoate, sodium acetate, sodium chloride, and the like. Lubricants are usually added at the very last step before tablet compression, since they must be present on the surfaces of the granules and in between them and the parts of the tablet press. The amount of lubricant in the composition can range, for example, from about 0.1 to about 5% by weight of the composition, from about 0.5 to about 2%, or from about 0.3 to about 1.5% by weight. The amount of compound or salt of the invention in a unit dose may be generally varied or adjusted from about 1.0 milligram to about 1,000 milligrams, from about 1.0 to about 900 milligrams, from about 1.0 to about 500 milligrams, or from about 1 to about 250 milligrams, according to the particular application and the potency of the compound. The actual dosage employed may be varied depending upon the patient's age, sex, weight and severity of the condition being treated.

Pharmaceutical compositions formulated for oral administration are often preferred. These compositions contain between 0.1 and 99% of a compound of the invention and usually at least about 5% (weight %) of a compound of the invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, tinctures, syrups, or elixirs, for example. Moreover, formulations containing these compounds can be presented as a dry product, e.g. as granules or powders, for constitution with water or other suitable vehicle before use. Typical components of carriers for syrups, elixirs, emulsions and suspensions include ethanol, glycerol, propylene glycol, polyethylene glycol, liquid sucrose, sorbitol and water. Liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid). Oral formulations may contain demulcent, flavoring agents, sweetening agents, such as sucrose or saccharin, taste-masking agents, and coloring agents.

Suspensions

Aqueous suspensions contain the active material(s) in admixture with excipients suitable for the manufacture of aqueous suspensions. Such excipients are suspending agents, for example AVICEL RC-591, sodium carboxymethylcellulose, methylcellulose, hydropropylmethylcellulose, sodium alginate, polyvinylpyrrolidone, gum tragacanth and gum acacia; dispersing or wetting agents, for example lecithin and polysorbate 80. The aqueous suspensions may also contain one or more preservatives, for example ethyl, n-propyl p-hydroxybenzoate, methyl parabens, propyl parabens, and sodium benzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard or soft shell capsules. A capsule is a dosage form provided in a special container or enclosure containing an active agent. The active agent may be present in solid, liquid, gel, or powder form, or any other pharmaceutically acceptable form. A capsule shell may be made of methyl cellulose, polyvinyl alcohols, or denatured gelatins or starch or other material. Hard shell capsules are typically made of blends of relatively high gel strength bone and pork skin gelatins. Soft shell capsule shells are often made of animal or plant gelatins. The capsule itself may contain small amounts of dyes, opaquing agents, plasticizers and preservatives.

The active agent in a capsule may be mixed with an inert solid diluent, for example, calcium carbonate, calcium phosphate or kaolin, or in the case of soft gelatin capsules the active ingredient may be mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be provided parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier typically comprises least about 90% by weight of the total composition.

Packaged Formulations

The invention includes packaged pharmaceutical combinations. Such packaged combinations include a compound of Formula I in a container. The container may additionally include instructions for using the combination to treat or prevent a viral infection, such as a hepatitis C infection, in a patient.

The packaged pharmaceutical combination may include one or more additional active agents.

Methods of Treatment

The invention includes methods of preventing and treating hepatitis C infections, by providing an effective amount of a compound of the invention to patient at risk for hepatitis C infection or infected with a hepatitis C virus.

The pharmaceutical combinations disclosed herein are useful for preventing and treating hepatitis C infections in patients. An effective amount of a pharmaceutical combination of the invention may be an amount sufficient to (a) prevent hepatitis C or a symptom of a hepatitis C from occurring in a patient who may be predisposed to hepatitis C but has not yet been diagnosed as having it or prevent diseases that may be associated with or caused by a primary hepatitis C infection (such as liver fibrosis that can result in the context of chronic HCV infection); (b) inhibit the progression of hepatitis C; and (c) cause a regression of the hepatitis C infection. An amount of a pharmaceutical composition effect to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

The invention also includes using pharmaceutical combinations comprising a compound of the invention and at least one additional active agent in prophylactic therapies. In the context of prophylactic or preventative treatment an effective amount of a compound of the invention is an amount sufficient to significantly decrease the patient's risk of contracting a hepatitis C infection.

Methods of treatment include providing certain dosage amounts of a compound of the invention and the at least one additional active agent to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage unit forms will generally contain between from about 1 mg to about 500 mg of each active agent. In certain embodiments 25 mg to 500 mg, or 25 mg to 200 mg of a compound of the invention are provided daily to a patient. When the additional active agent is NM 283 (valopicitabine), 100 mg to 1000 mg/day, or 200 mg to 800 mg/day, or 200 to 400 mg/day of either of those agents are typically provided to the patient. When the additional active agent is VX-950, 1000 mg to 3750 mg/day, or 1200 mg to 1800 mg/day are administered to the patient. Treatment regiments in which VX-950 is an additional active agent and about 350 to about 450 mg or about 700 to about 800 mg of VX-950 are administered to a patient three times per day or about 350 to about 450 mg or about 700 to about 800 mg is administered every 12 hours are particularly included in the invention.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Combination Methods

The invention includes methods of treatment in which a compound or salt of the invention is provided together with one or more additional active agents. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo. In certain embodiments the second active agent is ribavirin, interferon, or Peg-interferon alpha conjugate According to the methods of the invention, the compound of the invention and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound of The invention and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments method of treatment includes providing a patient with a compound of Formula I and an interferon such as a pegylated interferon or interferon gamma. The interferon may be the only compound provided with the compound of the invention or may be provided with an additional active agent that is not an interferon.

The invention methods of treatment and pharmaceutical combinations including compounds of the invention any one or combination of the following compounds and substances as an additional active agent:

Caspase inhibitors: IDN 6556 (Idun Pharmaceuticals)

Cyclophilin Inhibitors: NIM811 (Novartis) and DEBIO-025 (Debiopharm)

Cytochrome P450 monooxygenase inhibitors: ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole Glucocorticoids: hydrocortisone, cortisone, prednisone, prednisolone, methylprednisolone, triamcinolone, paramethasone, betamethasone, and dexamethasone Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, *ginseng*, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha n1 from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), unpegylated interferon alpha, alpha interferon, and its analogs, and synthetic thymosin alpha 1 (ZADAXIN, SciClone Pharmaceuticals Inc.)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmceuticals)

Nucleoside analogues: Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), and viramidine (Valeant Pharmaceuticals), an amidine prodrug of ribavirin. Combinations of nucleoside analogues may also be employed.

Non-nucleoside inhibitors: PSI-6130 (Roche/Pharmasset), delaviridine (RESCRIPTOR, Pfizer), and HCV-796 (Viropharm)

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex) and combinations comprising one or more of the foregoing protease inhibitors RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/ Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis) TLR agonists: ANA-975 (Anadys Pharmaceuticals), TLR7 agonist (Anadys Pharmaceuticals), CPG10101 (Coley), and TLR9 agonists including CPG 7909 (Coley)

Cyclophilin Inhibitors: NIM811 (Novartis) and DEBIO-025 (Debiopharm)

Patients receiving hepatitis C medications are typically given interferon together with another active agent. Thus methods of treatment and pharmaceutical combinations in which a compound of The invention is provided together with an interferon, such as pegylated interferon alfa 2a, as the additional active agents are included as embodiments. Similarly methods and pharmaceutical combinations in which ribavirin is an additional active agent are provided herein.

EXAMPLES

Abbreviations

The following chemical abbreviations are used in Example 1. Additional abbreviations used in these examples will be familiar to those of skill in the art of organic chemical synthesis.

CDI 1,1'-Carbonyldiimidazole
DBU Diazabicyclo[5.4.0]undec-7-ene
DCM Dichloromethane
DIEA N, N-Diisopropylethyl amine
DMF Dimethyl formamide
HATU O-(7-azabenotriazol-1-yl)-1,1,3,3-tetramethyluronium
HBTU O-(1H-Benzotriazol-1-yl) N, N,N',N'-tetramethyluronium hexafluorophosphate
NMM N-methylmorpholine
RCM Ring-closing metathesis
TEA Triethylacetate
TFA Trifluoroacetic acid Example 1

Synthesis of 1-((2S,4R)-1-((S)-2-tert-butyl-4-oxo-4-(piperidin-1-yl)butanoyl)-4-(7-methoxy-2-phenylquinolin-4-yloxy)pyrrolidine-2-carboxamido)-2-vinylcyclopropanecarboxylic acid Step 1. Preparation of N-(cyclopropylsulfonyl)-1-(BOC-amino)-2-vinylcyclopropanecarboxamide

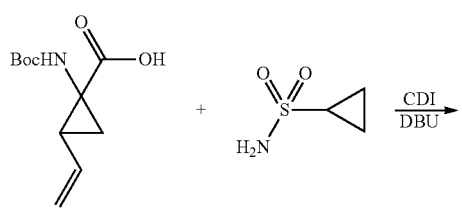

-continued

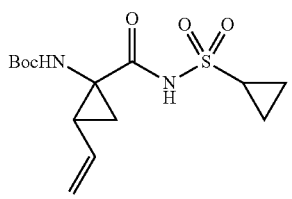

2

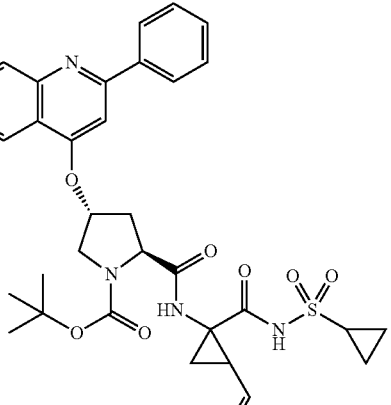

3

CDI (2.98 g, 18.4 mm, 1.1 eq) is dissolved in ethyl acetate. N-Boc-cyclopropylvinyl acid (3.8 g, 16.7 mm, 1.0 eq), prepared via the procedure given by Beaulieu, P. L. et al. (J. Org. Chem. 70: 5869-79 (2005)) is added to the CDI/ethyl acetate mixture and stirred at RT until the starting material is consumed. Cyclopropyl sulfonamine (2.2 g, 18.4 mm, 1.1 eq) is added to this mixture followed by DBU (2.1 ml, 20.5 mm, 1.23 eq) and the mixture is stirred at RT for 2 h. Workup and purification by silica gel chromatography provides 2 g of compound 2.

Step 2. Preparation of (2S,4R)-tert-butyl 2-(1-(cyclopropylsulfonylcarbamoyl)-2-vinylcyclopropylcarbamoyl)-4-(7-methoxy-2-phenylquinolin-4-yloxy)pyrrolidine-1-carboxylate and (2S,4R)—N-(1-(cyclopropylsulfonylcarbamoyl)-2-vinylcyclopropyl)-4-(7-methoxy-2-phenylquinolin-4-yloxy)pyrrolidine-2-carboxamide

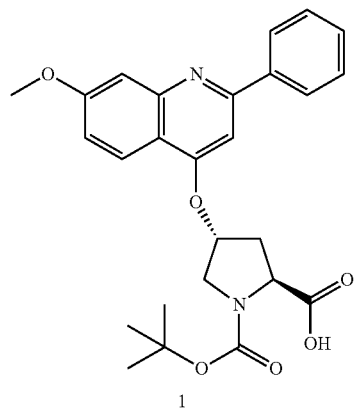

1

+

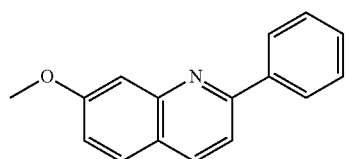

2

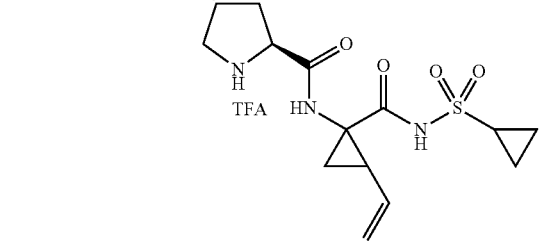

4

Compound 1 (4.3 g, 9.3 mmol, 1.1 eq), prepared according to the method given ins WO 02/060926, in DMF is stirred with O-(Benzotriazol-1yl)-N,N,N',N'-Tetramethyluronium hexafluorophosphate (4.1 g, 10.5 mmol, 1.3 eq) for 30 minutes, followed by addition of cyclopropylamine 2 (1.92 g, 8.3 mmol, 1.0 eq) and N-methylmorpholine (2.52 g, 25.0 mmol, 3.0 eq). The mixture is stirred over night and the solvent removed under reduced pressure. The resulting residue is diluted with ethyl acetate and washed with saturated aqueous $NaHCO_3$. The organic solvent is dried over $MgSO_4$ and concentrated under reduced pressure to afford crude 3, which is used for next step without further purification.

Compound 3 in 10 ml dry $CH_2Cl_2$ is treated with 5 mL TFA and stirred over night. The solvent is removed and the residue recrystallized from ethyl acetate to afford 4.12 g Compound 4 (61% yield two steps).

Step 3. Preparation of (3S)-3-((2S,4R)-2-(1-(cyclo-propylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoic acid

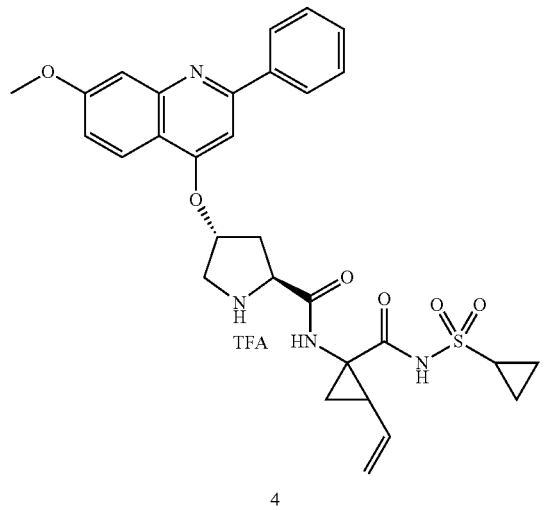

4

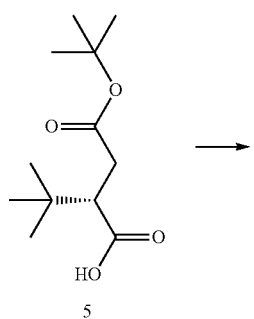

5

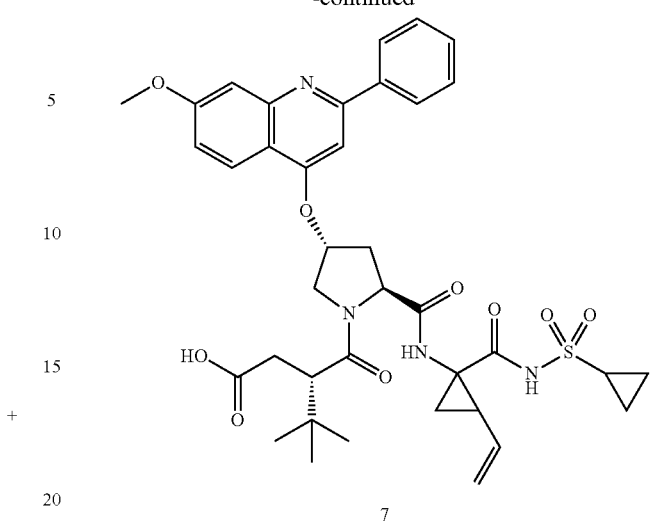

7

The Acid 5 (58 mg, 0.25 mmol, 1.2 eq), prepared via the procedure given by Evans, D. A., et al. (J. Org. Chem. 64: 6411-6417 (1999)) in 1.2 mL DMF is stirred with 4 (138 mg, 0.21 mmol), HATU (160 mg, 0.42 mmol, 2.0 eq), and DIEA (0.63 mmol, 3.0 eq) overnight. The mixture is subjected to HPLC purification to afford 121 mg 6 (77% yield), which is further treated with 0.5 mL TFA in 1.0 mL DCM overnight. The solvent was removed to provide Compound 7 in 100% yield.

Step 4. Preparation of (2S,4R)-1-((S)-2-tert-butyl-4-oxo-4-(piperidin-1-yl)butanoyl)-N-(1-(cyclopropyl-sulfonylcarbamoyl)-2-vinylcyclopropyl)-4-(7-methoxy-2-phenylquinolin-4-yloxy)pyrrolidine-2-carboxamide

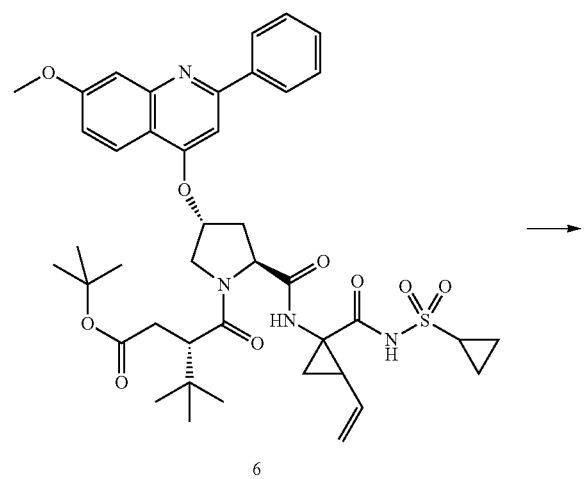

6

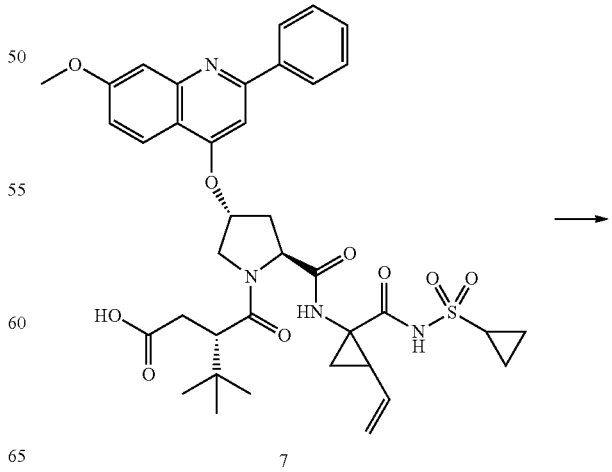

7

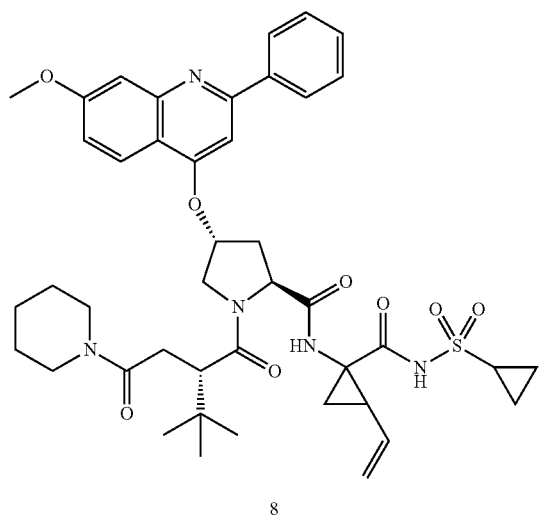

8

The Acid 7 (0.15 mmol) in 1.0 mL DMF is stirred with piperidine (excess, 0.6 mmol, 4 eq), HATU (115 mg, 0.3 mmol, 2.0 eq), and DIEA (0.45 mmol, 3.0 eq) for 4 hrs. The mixture is subjected to HPLC purification to afford 77.1 mg 8.

Step 5. Preparation of (3 S)-3-((2S,4R)-2-(1-(ethoxycarbonyl)-2-vinylcyclopropylcarbamoyl)-4-(7-methoxy-2-phenylquinolin-4-yloxy)pyrrolidine-1-carbonyl)-4,4-dimethylpentanoic acid

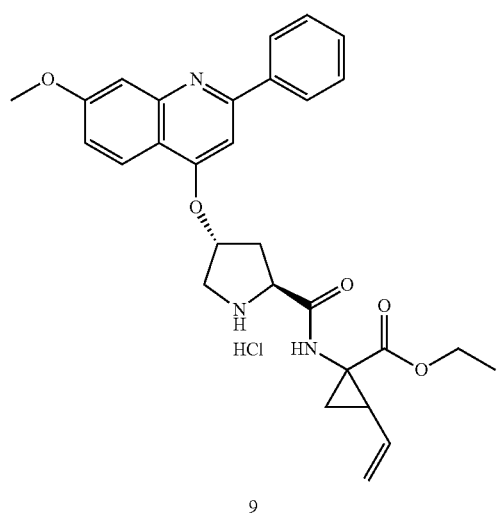

9

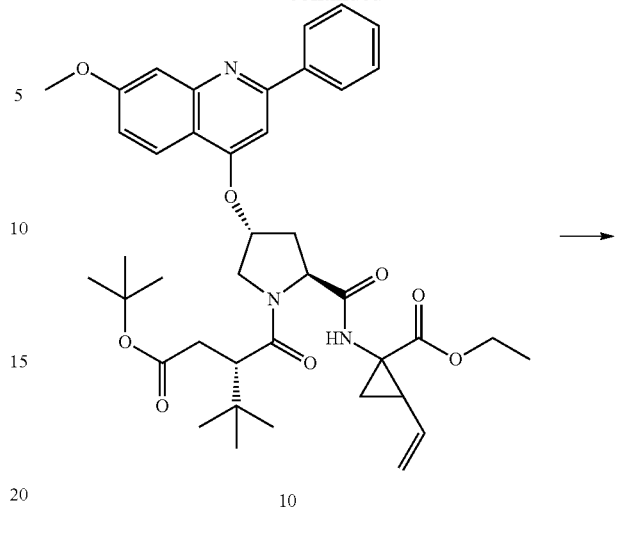

10

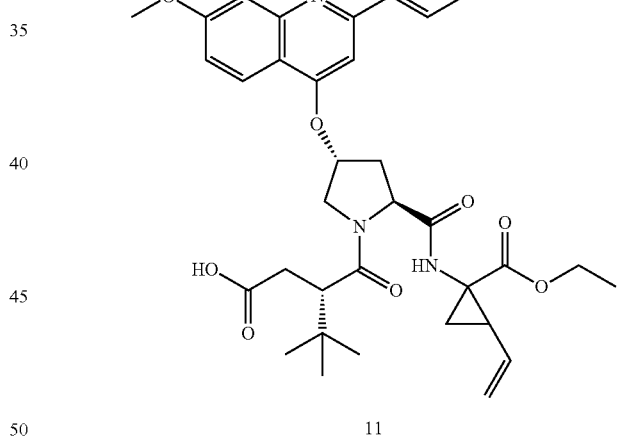

11

Step 5. Preparation of (3S)-3-((2S,4R)-2-(1-(ethoxycarbonyl)-2-vinylcyclopropylcarbamoyl)-4-(7-methoxy-2-phenylquinolin-4-yloxy)pyrrolidine-1-carbonyl)-4,4-dimethylpentanoic acid The Acid 5 (105 mg, 0.46 mmol, 1.2 eq) in 1.2 mL DMF is stirred with 9 (202 mg, 0.38 mmol), HATU (290 mg, 0.76 mmol, 2.0 eq), and DIEA (1.2 mmol, 3.0 eq) overnight. The mixture is subjected to HPLC purification to afford 204.3 mg 10 (75% yield), which is further treated with 0.5 mL TFA in 1.0 mL DCM overnight. The solvent is removed to provide 11 in 100% yield.

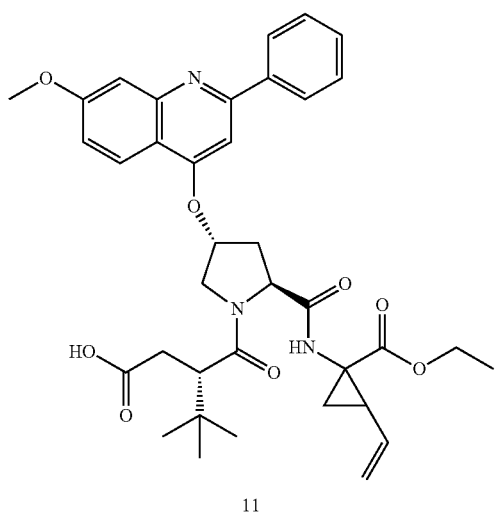

Step 6. Preparation of Final Product

The Acid 11 (30 mg, 0.045 mmol) in 1.0 mL DMF is stirred with piperidine (0.27 mmol, 6 eq), HATU (34 mg, 0.09 mmol, 2.0 eq), and DIEA (0.14 mmol, 3.0 eq) for 2 hrs. The mixture is subjected to HPLC purification to afford 21.2 mg 12 (65% yield), which is hydrolyzed in methanol with 2N NaOH for 6 hrs. The mixture is acidified with 6N HCl and subjected to HPLC purification to afford 7.6 mg 13.

Example 2

Synthesis of Macrocyclic Compounds

General Procedures

Procedure 1. DeProtection Reaction (Conversion of N-Boc to Amine or t-Butyl Ester to Carboxylic Acid)

TFA (3~4 ml) is added to a solution of Boc protected starting material (1 mmol) or t-butyl ester in anhydrous DCM (7 ml) at room temperature. The reaction is monitored with LC/MS and TLC. After 1~3 hrs, the reaction mixture is evaporated reduced pressure to dryness. The crude product is used for next step reaction without further purification.

Procedure 2. Amide Formation

N-methylmorpholine (2 mmol) and HBTU (1.2 mmol) are added in one portion at room temperature to a solution of acid (1 mmol) in anhydrous DMF (10 ml). After stirring at room temperature 10 minutes, amine (1 mmol) is added in one portion and then stirred overnight. The reaction mixture is poured into ice-water and extracted with ethyl acetate (100 ml). The organic layer is washed with $H_2O$, brine, and dried over anhydrous $MgSO_4$. The residue is filtered and evaporated in vacuum to dryness. The crude product is purified by flash chromatography on silica gel (hexane-ethyl acetate 100:0 to 50:50) to give the desired product.

Procedure 3. RCM catalyzed by Grubbs $2^{nd}$ (CAS Reg. No. 246047-72-3) or Hoveyda-Grubbs $2^{nd}$ catalyst (CAS Reg. No. 301224-40-8)

A mixture of starting material (di-olefin, 1 mmol), catalyst (5~30 mol %) in 1,2-dichloroethane is degassed and heated to 110° C. for 12~24 hrs under atmosphere of argon. The reaction is monitored by LC/MS and TLC. The reaction mixture is evaporated to dryness under reduced pressure. The crude product is purified by flash chromatography on silica gel (hexane-ethyl acetate 100:0 to 50:50) to give the desired product.

Procedure 4. Hydrolysis of Esters

LiOH hydrate (6 equiv.) is added in one portion at room temperature to the solution of ester (1 mmol) in THF (5 ml), methanol (2.5 ml), and water (2.5 ml), and then the reaction mixture is stirred overnight. After the reaction is complete (by LC/MS), it is cooled to 0° C. and acidified to pH~2 and extracted with DCM (20 ml x 2). The reaction is dried over $MgSO_4$, filtered, and evaporated to dryness under reduced pressure. The crude product is purified by flash chromatography on silica gel (hexane-ethyl acetate 100:0 to 20:80) to give the desired product.

Scheme 1
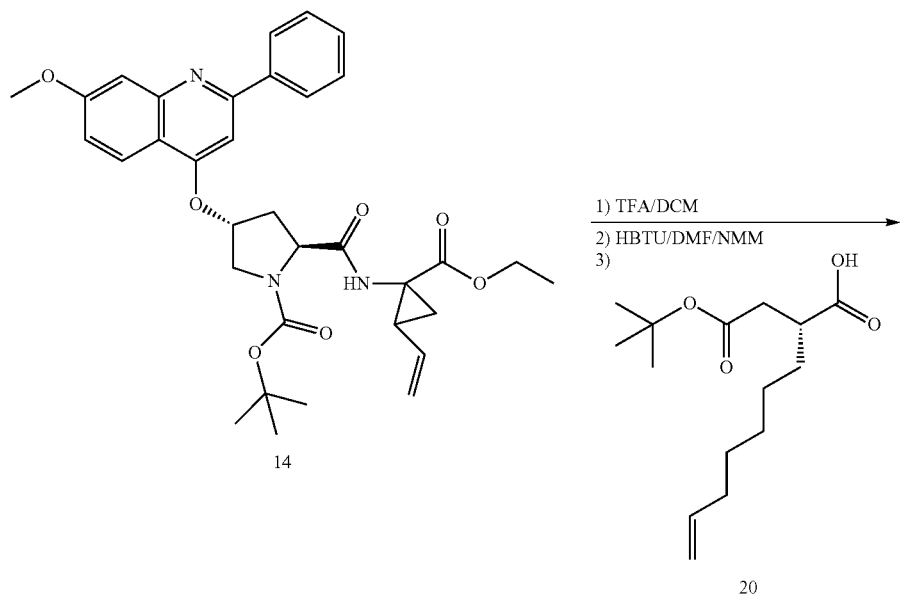
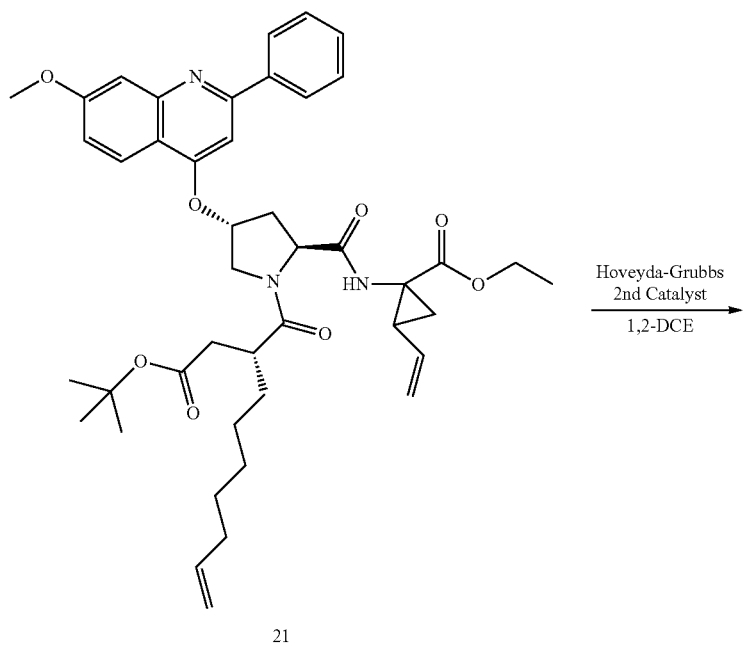

-continued
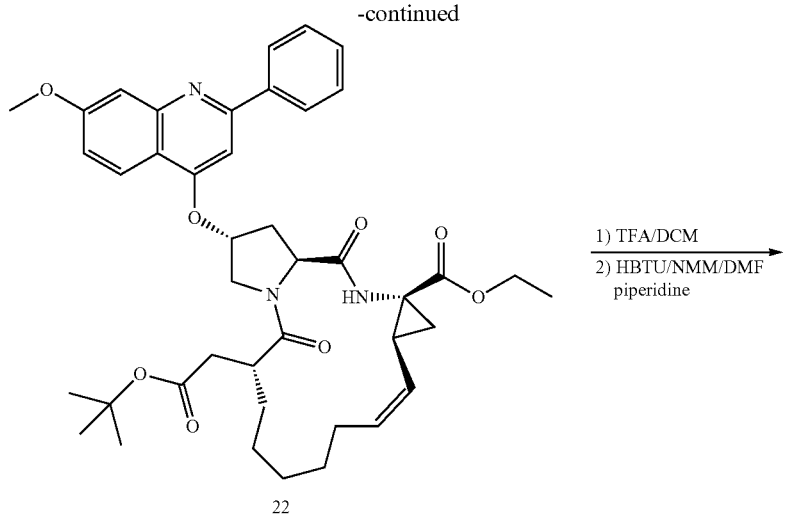
22
1) TFA/DCM
2) HBTU/NMM/DMF piperidine
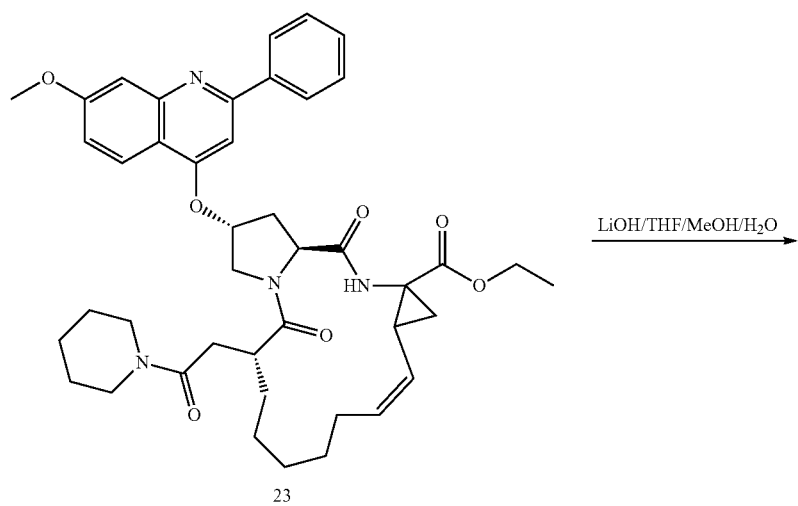
23
LiOH/THF/MeOH/H$_2$O
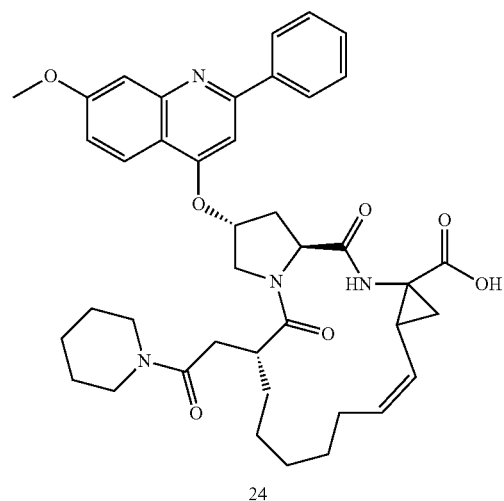
24
Compound 21 is prepared by procedures 1 and 2 from starting material 14 and amino acid 20. MS (M$^+$+1) 754.
Compound 22 is prepared by procedure step 3. MS (M$^+$+1) 726.
Compound 23 is prepared by procedures 1 and 2. MS (M$^+$+1) 737.
Compound 24 is prepared by procedure 4. MS (M$^+$+1) 709.

Scheme 2. Synthesis of Compounds 34 and 35
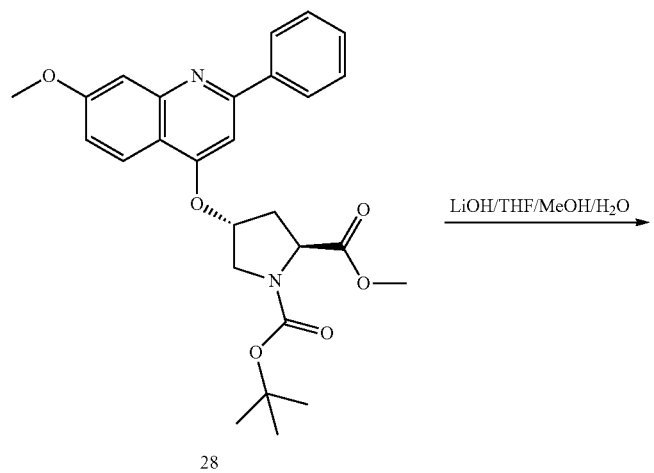
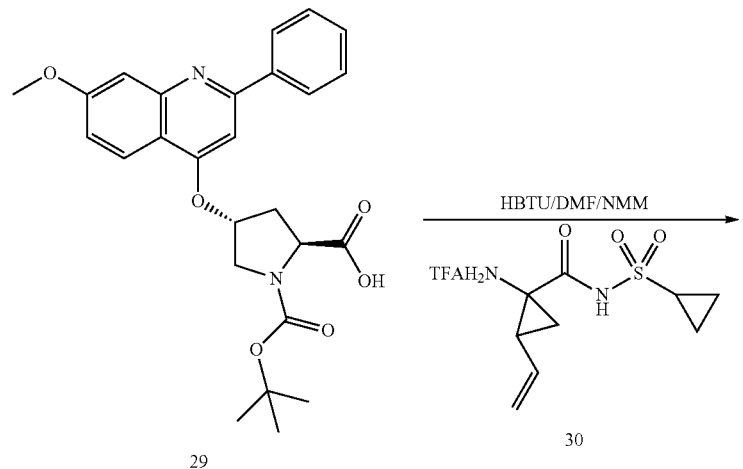
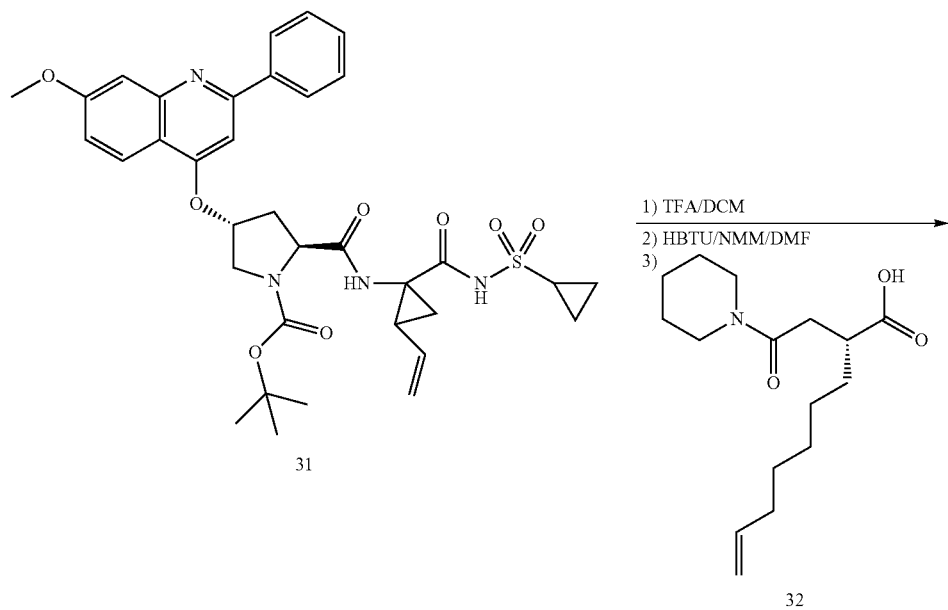

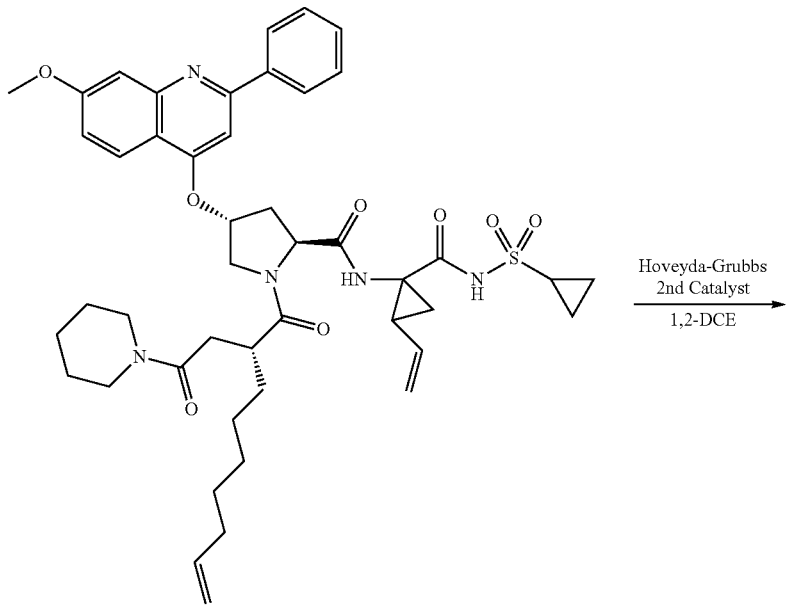
33
Hoveyda-Grubbs 2nd Catalyst
1,2-DCE
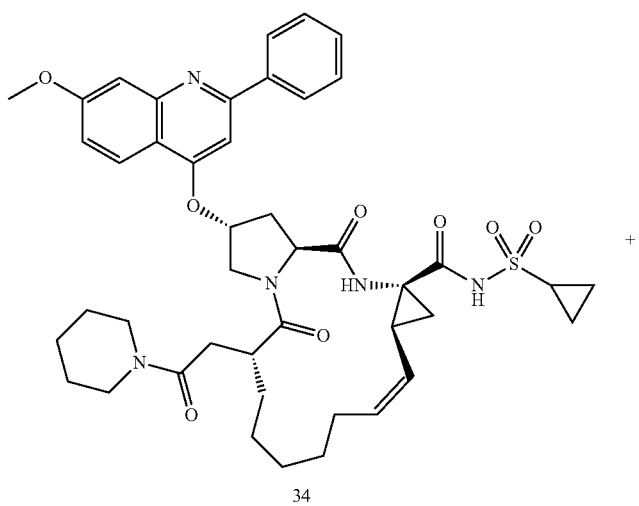
34
+
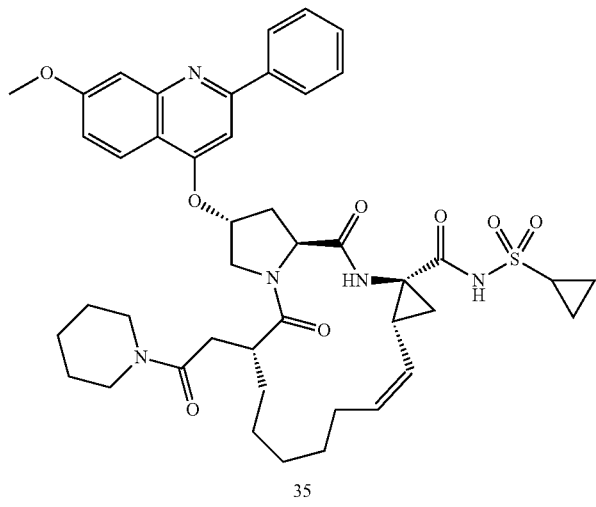
35

Compound 29 is prepared by procedure 4 from starting material 28.

Compound 30 is prepared by procedure set forth in step 2 with starting material 29.

Compound 31 is prepared by procedure set forth in steps 1 and 2 with starting material 30.

Compound 33 is prepared by procedure set forth in step 4 with starting material 28 and 32.

Compounds 34 and 35 are prepared by the procedure set forth in step 3. After RCM, the reaction mixture is separated by prep-TLC (hexane-ethyl acetate 1:1) to afford compounds 34 and 35. MS (M$^+$+1)=812

Preparation of Intermediates 20 and 32

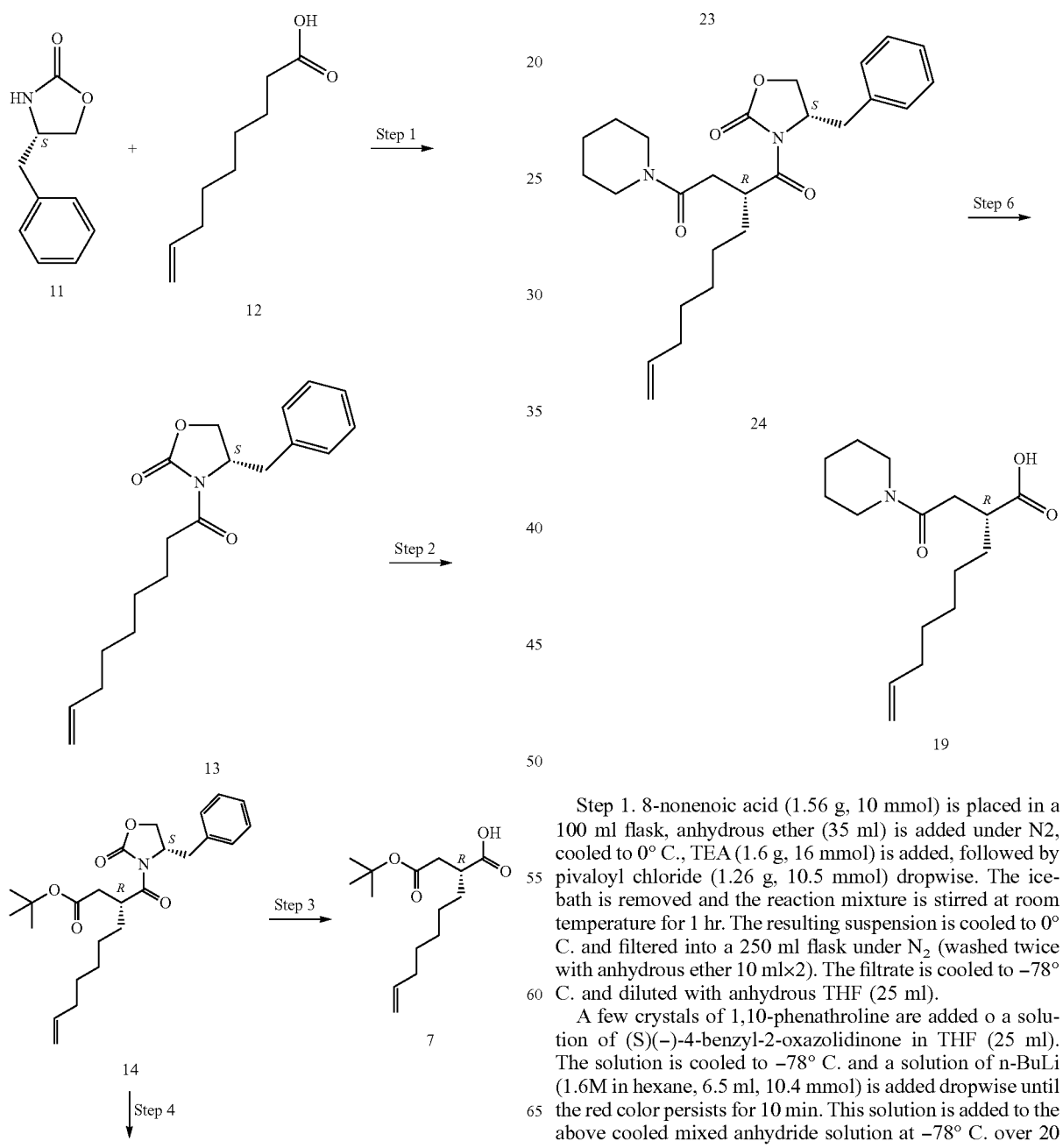

Step 1. 8-nonenoic acid (1.56 g, 10 mmol) is placed in a 100 ml flask, anhydrous ether (35 ml) is added under N2, cooled to 0° C., TEA (1.6 g, 16 mmol) is added, followed by pivaloyl chloride (1.26 g, 10.5 mmol) dropwise. The ice-bath is removed and the reaction mixture is stirred at room temperature for 1 hr. The resulting suspension is cooled to 0° C. and filtered into a 250 ml flask under N$_2$ (washed twice with anhydrous ether 10 ml×2). The filtrate is cooled to −78° C. and diluted with anhydrous THF (25 ml).

A few crystals of 1,10-phenathroline are added o a solution of (S)(−)-4-benzyl-2-oxazolidinone in THF (25 ml). The solution is cooled to −78° C. and a solution of n-BuLi (1.6M in hexane, 6.5 ml, 10.4 mmol) is added dropwise until the red color persists for 10 min. This solution is added to the above cooled mixed anhydride solution at −78° C. over 20 min via cannula. The resulting mixture is stirred at −78° C.

for additional 30 min, then poured into sat. NH₄C₁, the organic layer is separated, the aqueous layer is extracted with ether (50 ml, 3×). The combined organic layers are washed with brine and dried over MgSO₄, filtered, concentrated in reduced pressure to dryness. The crude product is purified by flash chromatography (hexane-ethyl acetate 100:0~100:20) to give 3.01 g of 26 (95%).

Step 2. A solution of 26 (3.01 g, 9.6 mmol) in anhydrous THF is cooled to −78° C., then 2.0 m solution of NaN(TMS)₂ in hexane (5.76 ml) was added dropwise over 10 min. After 30 min, t-Butyl bromoacetate was added dropwise at −78° C. The reaction mixture was stirred at −78° C. for 2 hrs. LC/MS and TLC monitored the reaction. The reaction was quenched with 10% KHSO₄ to pH~4~6, extracted with ethyl acetate, organic layer was washed with H₂O, brine, dried over MgSO₄, filtered, evaporated in reduced pressure to dryness. The crude product was purified by chromatography on silica gel (hexane-ethyl acetate 100:0~100:20) to give compound 14.

Step 3. H₂O₂ (50%, 0.9 ml) is added dropwise over 5 min. at 0° C., followed by a solution of LiOH (0.2 g in 2 ml of H₂O). The reaction mixture is added to a solution of 27 (1.05 g, 2.44 mmol) in THF/H2O (5:1, 24 ml). The mixture is stirred at 0° C. for 1 h and then quenched by dropwise addition of an aqueous solution of sodium thiosulphate (10 ml) while keeping the temperature below 20° C. The mixture is extracted with ethyl acetate (discarded) and the aqueous phase was acidified to pH~2 with solid citric acid and extracted with ethyl acetate. The combined organic phase is washed with brine, dried over anhydrous sodium sulphate and the solvent removed under reduced pressure. The residue is purified by column chromatography on silica gel, eluting with a gradient system of hexane:ethyl acetate (100:0) to 50:50 to afford the desired compound 20 (503 mg).

Step 4. Compound 36 is prepared by procedure 1.
Step 5. Compound 37 is prepared by procedure 2.
Step 6. Compound 32 is prepared from 37 by the procedure given in step 3 for the preparation of compound 20.

Example 3

Additional Tertiary Amine Substituted Peptides

| No. | STRUCTURE | Name | EC50 |
|---|---|---|---|
| 38 | 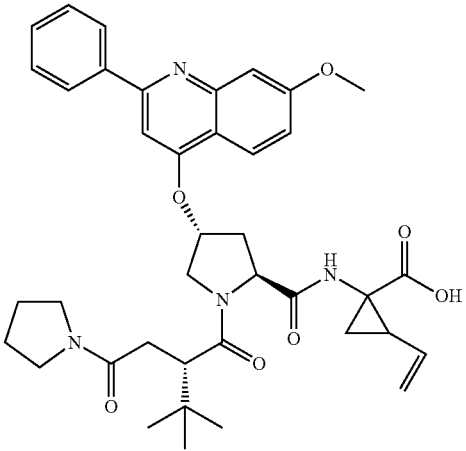 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCC1)C(C)(C)C)C(=O)O] | 1-((2S,4R)-1-((S)-2-tert-butyl-4-oxo-4-(pyrrolidin-1-yl)butanoyl)-4-(7-methoxy-2-phenylquinolin-4-yloxy)pyrrolidine-2-carboxamido)-2-vinylcyclopropanecarboxylic acid | * |
| 39 | 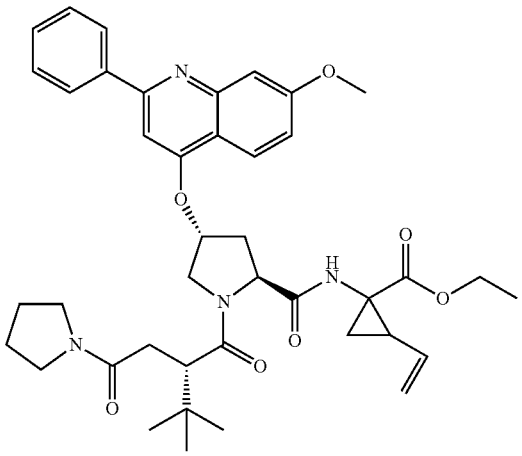 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCC1)C(C)(C)C)C(=O)OCC] | ethyl 1-((2S,4R)-1-((S)-2-tert-butyl-4-oxo-4-(pyrrolidin-1-yl)butanoyl)-4-(7-methoxy-2-phenylquinolin-4-yloxy)pyrrolidine-2-carboxamido)-2-vinylcyclopropanecarboxylate | * |

| No. | STRUCTURE | Name | EC50 |
|---|---|---|---|
| 40 | 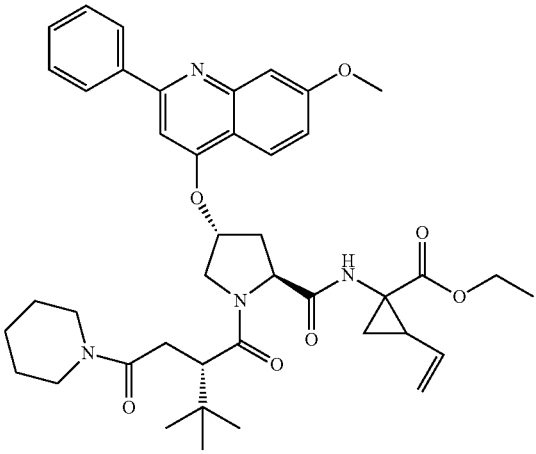 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)OCC] | ethyl 1-((2S,4R)-1-((S)-2-tert-butyl-4-oxo-4-(piperidin-1-yl)butanoyl)-4-(7-methoxy-2-phenylquinolin-4-yloxy)pyrrolidine-2-carboxamido)-2-vinylcyclopropanecarboxylate | * |
| 41 | 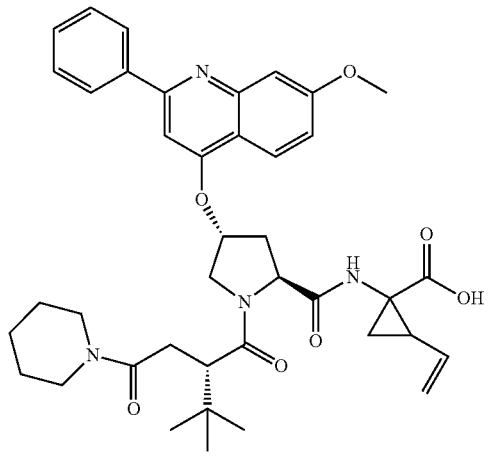 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)O] | 1-((2S,4R)-1-((S)-2-tert-butyl-4-oxo-4-(piperidin-1-yl)butanoyl)-4-(7-methoxy-2-phenylquinolin-4-yloxy)pyrrolidine-2-carboxamido)-2-vinylcyclopropanecarboxylic acid | ** |
| 42 | 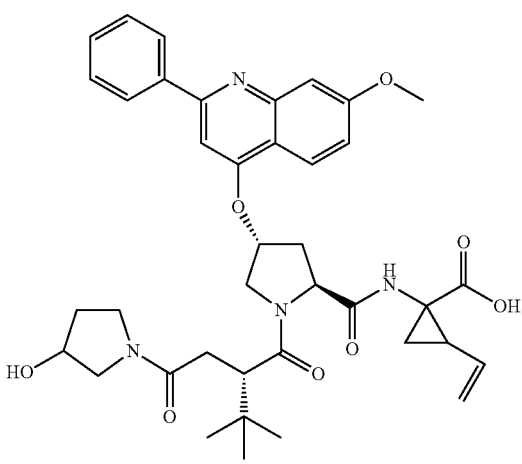 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCC(O)C1)C(C)(C)C)C(=O)O] | 1-((2S,4R)-1-((2S)-2-tert-butyl-4-(3-hydroxypyrrolidin-1-yl)-4-oxobutanoyl)-4-(7-methoxy-2-phenylquinolin-4-yloxy)pyrrolidine-2-carboxamido)-2-vinylcyclopropanecarboxylic acid | * |

-continued

| No. | STRUCTURE | Name | EC50 |
|---|---|---|---|
| 43 | 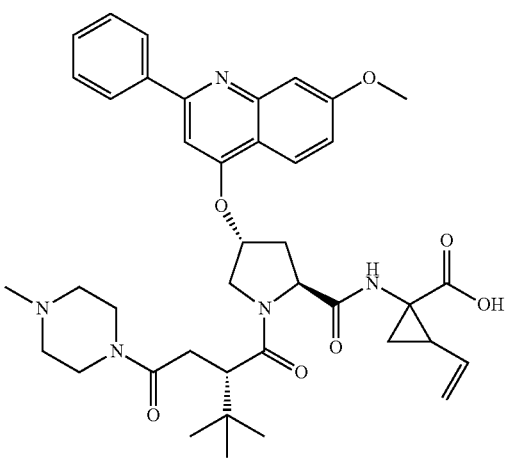 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCN(C)CC1)C(C)(C)C)C(=O)O] | 1-((2S,4R)-1-((S)-2-tert-butyl-4-(4-methylpiperazin-1-yl)-4-oxobutanoyl)-4-(7-methoxy-2-phenylquinolin-4-yloxy)pyrrolidine-2-carboxamido)-2-vinylcyclopropanecarboxylic acid | * |
| 44 | 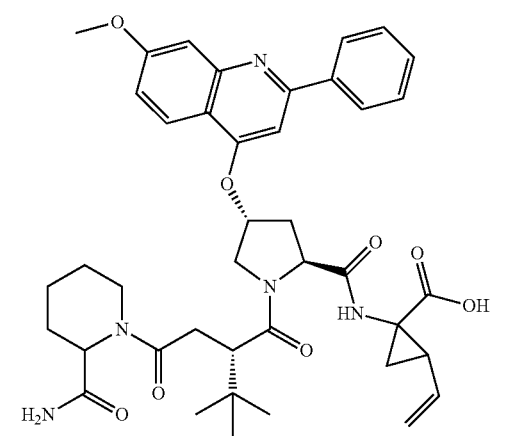 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1C(N)=O)C(C)(C)C)C(=O)O] | 1-((2S,4R)-1-((2S)-2-tert-butyl-4-(2-carbamoylpiperidin-1-yl)-4-oxobutanoyl)-4-(7-methoxy-2-phenylquinolin-4-yloxy)pyrrolidine-2-carboxamido)-2-vinylcyclopropanecarboxylic acid | * |
| 45 | 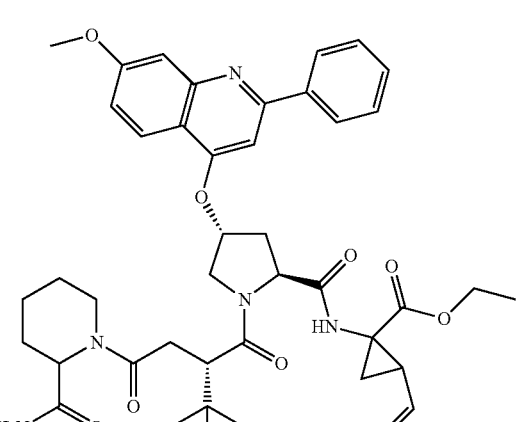 | ethyl 1-((2S,4R)-1-((2S)-2-tert-butyl-4-(2-carbamoylpiperidin-1-yl)-4-oxobutanoyl)-4-(7-methoxy-2-phenylquinolin-4-yloxy)pyrrolidine-2-carboxamido)-2-vinylcyclopropanecarboxylate | ** |

| No. | STRUCTURE | Name | EC50 |
|---|---|---|---|
| 46 | 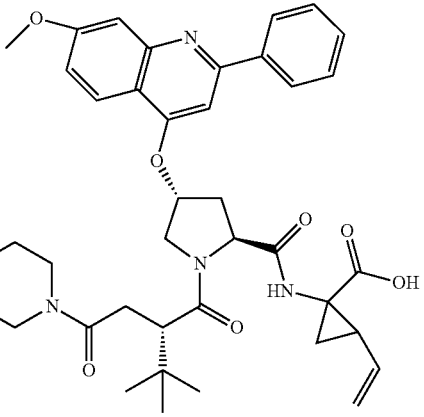 | 1-((2S,4R)-1-((S)-4-(4-((tert-butoxycarbonylamino)methyl)piperidin-1-yl)-2-tert-butyl-4-oxobutanoyl)-4-(7-methoxy-2-phenylquinolin-4-yloxy)pyrrolidine-2-carboxamido)-2-vinylcyclopropanecarboxylic acid | * |
| 47 | 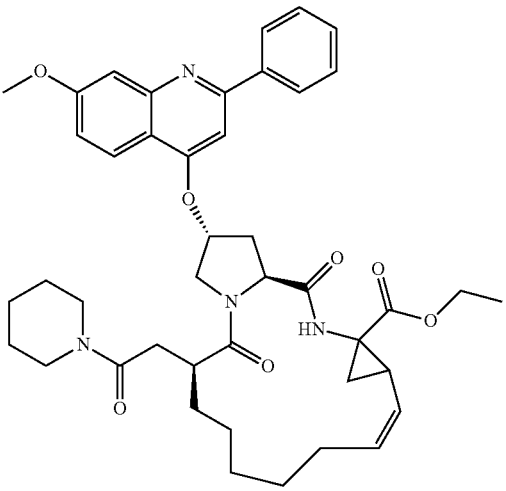 [SMILES: CCOC(=O)C12CC1/C=C\CCCCC[C@@H](CC(=O)N1CCCCC1)C(=O)N1C[C@H](Oc3cc(-c4ccccc4)nc4cc(OC)ccc34)C[C@H]1C(=O)N2] | (2R,6S,16aS,Z)-ethyl 2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate | ** |
| 48 | 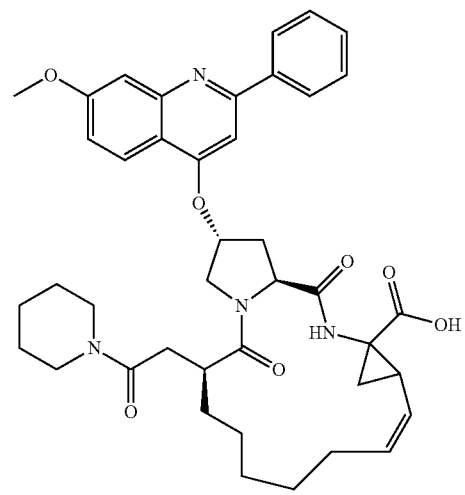 [SMILES: COc1ccc2c(O[C@@H]3C[C@H]4C(=O)NC5(C(=O)O)CC5/C=C\CCCCC[C@@H](CC(=O)N5CCCCC5)C(=O)N4C3)cc(-c3ccccc3)nc2c1] | (2R,6S,16aS,Z)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid | * |

| No. | STRUCTURE | Name | EC50 |
|---|---|---|---|
| 49 | 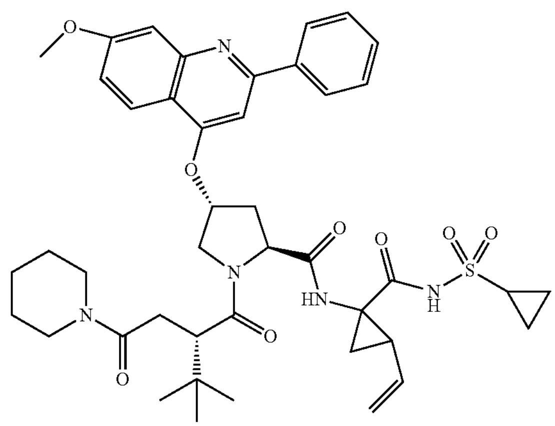 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-(1-(cyclopropylsulfonylcarbamoyl)-2-vinylcyclopropyl)-4-(7-methoxy-2-phenylquinolin-4-yloxy)pyrrolidine-2-carboxamide | *** |
| 50 | 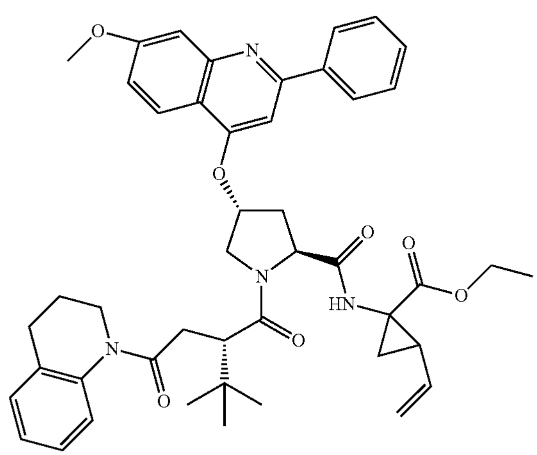 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCc2ccccc21)C(C)(C)C)C(=O)OCC] | ethyl 1-((2S,4R)-1-((S)-2-tert-butyl-4-(3,4-dihydroquinolin-1(2H)-yl)-4-oxobutanoyl)-4-(7-methoxy-2-phenylquinolin-4-yloxy)pyrrolidine-2-carboxamido)-2-vinylcyclopropanecarboxylate | ** |
| 51 | 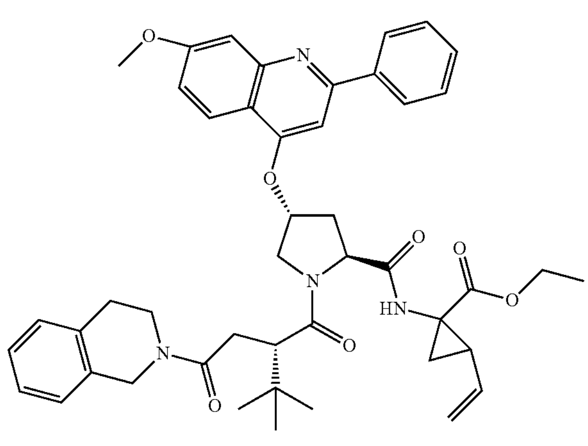 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCc2ccccc2C1)C(C)(C)C)C(=O)OCC] | ethyl 1-((2S,4R)-1-((S)-2-tert-butyl-4-(3,4-dihydroisoquinolin-2(1H)-yl)-4-oxobutanoyl)-4-(7-methoxy-2-phenylquinolin-4-yloxy)pyrrolidine-2-carboxamido)-2-vinylcyclopropanecarboxylate | * |

| No. | STRUCTURE | Name | EC50 |
|---|---|---|---|
| 52 | 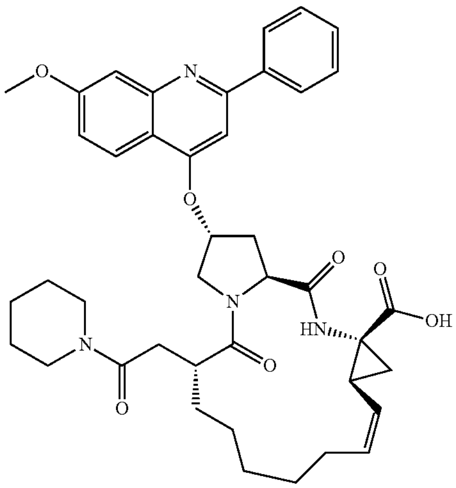 [SMILES: COc1ccc2c(O[C@@H]3C[C@H]4C(=O)N[C@]5(C(=O)O)C[C@H]5/C=C\CCCCC[C@H](CC(=O)N5CCCCC5)C(=O)N4C3)cc(-c3ccccc3)nc2c1] | (2R,6R,13aS,14aR,16aS,Z)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid | * |
| 53 | 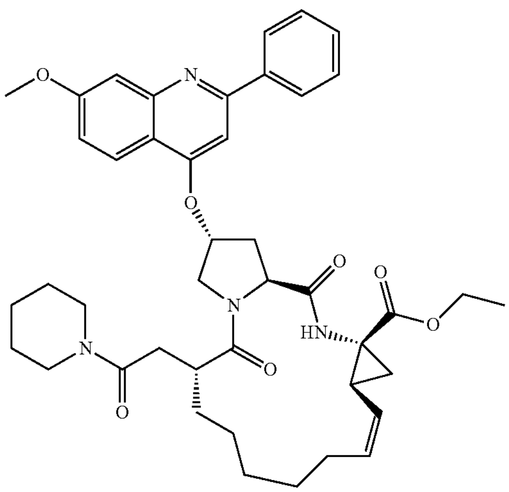 [SMILES: CCOC(=O)[C@@]12C[C@H]1/C=C\CCCCC[C@H](CC(=O)N1CCCCC1)C(=O)N1C[C@H](Oc3cc(-c4ccccc4)nc4cc(OC)ccc34)C[C@H]1C(=O)N2] | (2R,6R,13aS,14aR,16aS,Z)-ethyl 2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate | * |
| 54 | 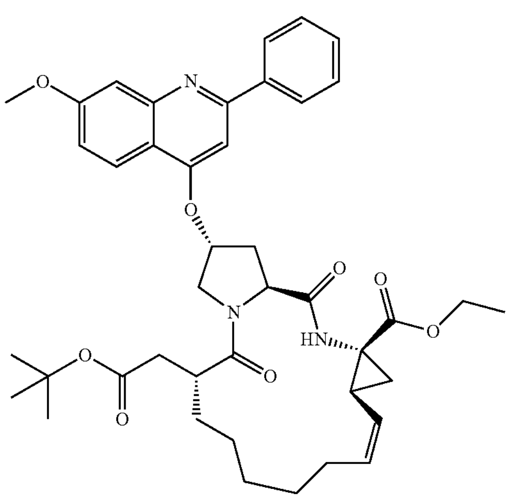 [SMILES: CCOC(=O)[C@@]12C[C@H]1/C=C\CCCCC[C@H](CC(=O)OC(C)(C)C)C(=O)N1C[C@H](Oc3cc(-c4ccccc4)nc4cc(OC)ccc34)C[C@H]1C(=O)N2] | (2R,6R,13aS,14aR,16aS,Z)-ethyl 6-(2-tert-butoxy-2-oxoethyl)-2-(7-methoxy-2-phenylquinolin-4-yloxy)-5,16-dioxo-1,2,3,5,6,7,8,9,10,11,13a,14,14a,15,16,16a-hexahydrocyclopropa[e]pyrrolo[1,2-a][1,4]diazacyclopentadecine-14a-carboxylate | * |

| No. | STRUCTURE | Name | EC50 |
|---|---|---|---|
| 55 | 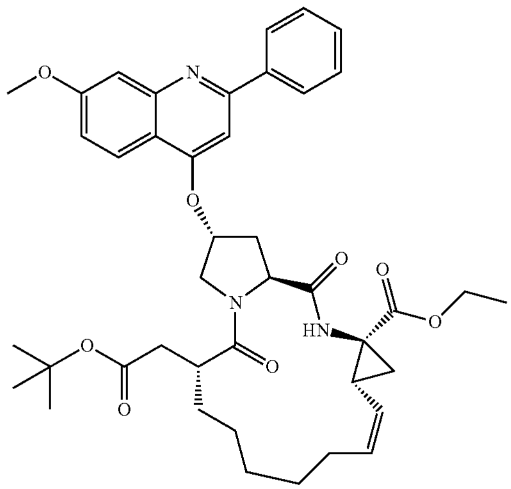 [SMILES: CCOC(=O)[C@]12C[C@@H]1/C=C\CCCCC[C@H](CC(=O)OC(C)(C)C)C(=O)N1C[C@H](Oc3cc(-c4ccccc4)nc4cc(OC)ccc34)C[C@H]1C(=O)N2] | (2R,6R,13aR,14aS,16aS,Z)-ethyl 6-(2-tert-butoxy-2-oxoethyl)-2-(7-methoxy-2-phenylquinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate | * |
| 56 | 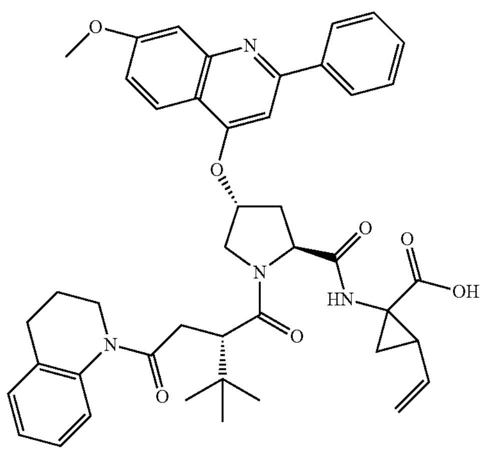 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCc2ccccc21)C(C)(C)C)C(=O)O] | 1-((2S,4R)-1-((S)-2-tert-butyl-4-(3,4-dihydroquinolin-1(2H)-yl)-4-oxobutanoyl)-4-(7-methoxy-2-phenylquinolin-4-yloxy)pyrrolidine-2-carboxamido)-2-vinylcyclopropanecarboxylic acid | ** |
| 57 | 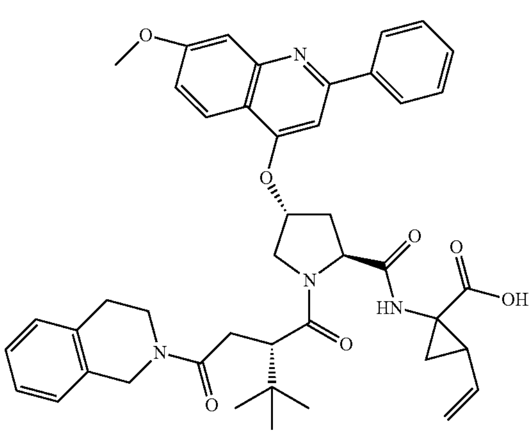 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCc2ccccc2C1)C(C)(C)C)C(=O)O] | 1-((2S,4R)-1-((S)-2-tert-butyl-4-(3,4-dihydroisoquinolin-2(1H)-yl)-4-oxobutanoyl)-4-(7-methoxy-2-phenylquinolin-4-yloxy)pyrrolidine-2-carboxamido)-2-vinylcyclopropanecarboxylic acid | * |

-continued

| No. | STRUCTURE | Name | EC50 |
|---|---|---|---|
| 58 | 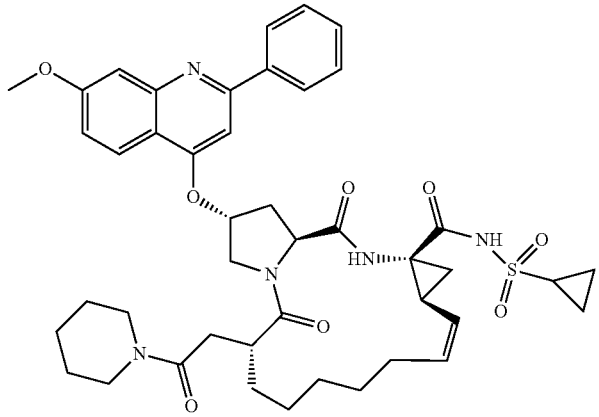 [SMILES: COc1ccc2c(O[C@@H]3C[C@H]4C(=O)N[C@]5(C(=O)NS(=O)(=O)C6CC6)C[C@H]5/C=C\CCCCC[C@H](CC(=O)N5CCCCC5)C(=O)N4C3)cc(-c3ccccc3)nc2c1] | (2R,6R,13aS,14aR,16aS,Z)-N-(cyclopropylsulfonyl)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide | *** |
| 59 | 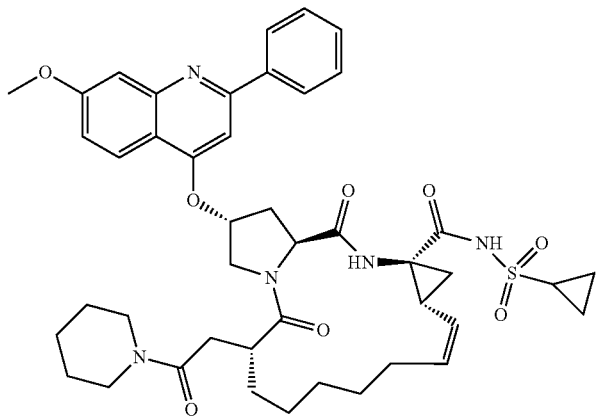 [SMILES: COc1ccc2c(O[C@@H]3C[C@H]4C(=O)N[C@@]5(C(=O)NS(=O)(=O)C6CC6)C[C@@H]5/C=C\CCCCC[C@H](CC(=O)N5CCCCC5)C(=O)N4C3)cc(-c3ccccc3)nc2c1] | (2R,6R,13aR,14aS,16aS,Z)-N-(cyclopropylsulfonyl)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide | *** |
| 60 | 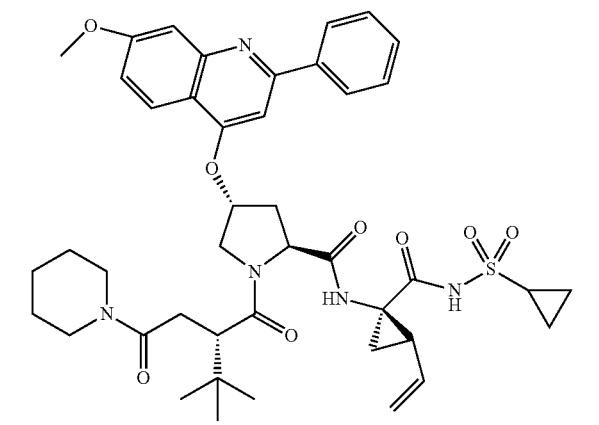 | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** |

Example 4

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

4A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

4B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N1 1, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×10$^5$ cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

4C. Treatment of HCV-Replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 fcells/100 μl/well of 96 well plate (6-7.5×10$^5$ cells/10 ml/plate). Plates are placed into 37° C. 5% $CO_2$ incubator overnight.

4D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 μl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 μl of PBS. The PBS is then decanted and the plates tapped in a paper towel to remove any remaining PBS. Cells are fixed in situ with 100 μl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

Compounds shown in Example 3 have been tested in this assay. Those with one "*" in the EC50 column have an EC50 greater than 10 micromolar, those with two 's () have an EC50 of greater than 1 micromolar but less than 10 micromolar, and compounds with three 's (*) have EC50 values of 100 nanomolar or less.

Example 5

Cytotoxicity Assays

To insure that the decrease in replicon replication is due to compound activity against the HCV replicon rather than nonspecific toxicity assays are used to quantitate compound cytotoxicity.

5A. Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

5B. MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 µl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Albumin and MTS methods for determining cytotoxicity may be obtained as follows: Cells are treated with different concentrations of test compound or Helioxanthin for a three day-period. Prior to lysis for detection albumin as described above, the MTS reagent is added according to manufacturer's instruction to each well and incubate at 37° C. and read at OD 490 nm. The cellular albumin quantitation is then performed as described above.

We claim:

1. A pharmaceutical composition comprising a therapeutically effective amount of a compound having the structure

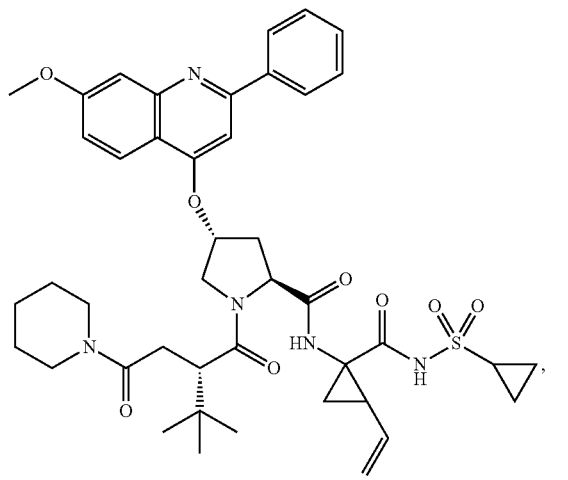 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1]

or a pharmaceutically acceptable salt thereof, and at least one pharmaceutically acceptable carrier.

2. A pharmaceutical composition comprising a therapeutically effective amount of a compound having the structure

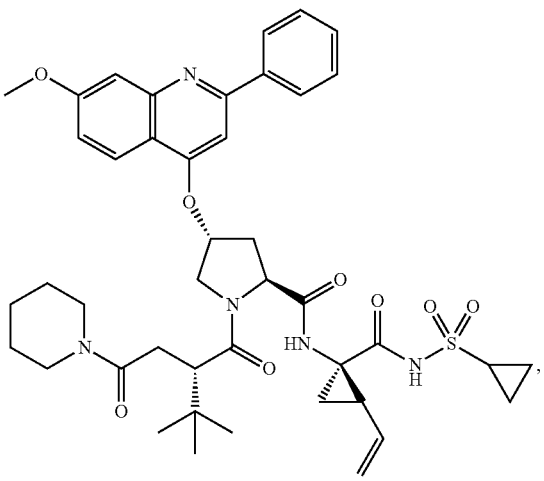

or a pharmaceutically acceptable salt thereof, and at least one pharmaceutically acceptable carrier.

3. A method of treating a hepatitis C infection in a patient, comprising providing a therapeutically effective amount of a compound having the structure

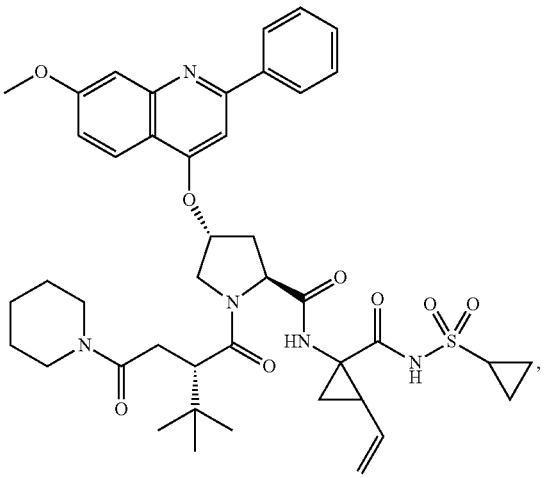 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1]

or a pharmaceutically acceptable salt thereof, and at least one pharmaceutically acceptable carrier.

4. The method of claim 3, wherein the patient is a human.

5. A method of treating a hepatitis C infection in a patient, comprising providing a therapeutically effective amount of a compound having the structure

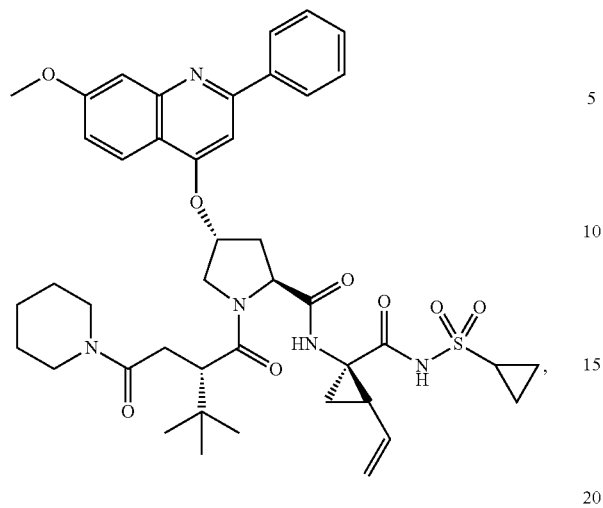
or a pharmaceutically acceptable salt thereof, and at least one pharmaceutically acceptable carrier.
6. The method of claim 5, wherein the patient is human.